(12) United States Patent
Allhorn et al.

(10) Patent No.: US 8,323,908 B2
(45) Date of Patent: Dec. 4, 2012

(54) METHOD OF ASSESSING GLYCOSYLATION STATE OR FUNCTIONAL QUALITY OF AN IGG CONTAINING SAMPLE

(75) Inventors: Maria Allhorn, Ramösa (SE); Anders Olin, Lund (SE); Falk Nimmerjahn, Erlangen (DE); Mattias Collin, Lund (SE)

(73) Assignee: Genovis AB, Lund (SE)

( * ) Notice: Subject to any disclaimer, the term of this patent is extended or adjusted under 35 U.S.C. 154(b) by 77 days.

(21) Appl. No.: 12/677,680

(22) PCT Filed: Sep. 11, 2008

(86) PCT No.: PCT/EP2008/007457
§ 371 (c)(1),
(2), (4) Date: Jun. 16, 2010

(87) PCT Pub. No.: WO2009/033670
PCT Pub. Date: Mar. 19, 2009

(65) Prior Publication Data
US 2010/0317083 A1 Dec. 16, 2010

Related U.S. Application Data

(60) Provisional application No. 60/960,087, filed on Sep. 14, 2007.

(51) Int. Cl.
*G01N 33/53* (2006.01)
(52) U.S. Cl. .................................................. 435/7.1
(58) Field of Classification Search .................. None
See application file for complete search history.

(56) References Cited

FOREIGN PATENT DOCUMENTS
WO  WO 91/19740       12/1991
WO  WO 03/051914 A2   6/2003
WO  WO 03/051914 A3   6/2003

OTHER PUBLICATIONS

Mikayama et al. PNAS, 1993. 90: 10056-10060.*
Burgess et al J Cell Biol. 111:2129-2138, 1990.*
Wang et al. JBC, 2001 276:49213-49220.*
Notification of Transmittal of the International Search Report and Written Opinion of the International Searching Authority from counterpart International Application No. PCT/EP2008/007457, dated Oct. 3, 2009.
Allhorn, M. et al., "Human IgG/FcγR Interactions Are Modulated by Streptococcal IgG Glycan Hydrolysis", *PlOs One*, 3(1): 1-12 (Jan. 2008).
Allhorn, M. et al., "EndoS from *Streptococcus pyogenes* is hydrolyzed by the cysteine proteinase SpeB and requires glutamic acid 235 and tryptophans for IgG glycan-hydrolyzing activity", *BMC Microbiology*, BioMed Central, 8(1): 1-10 (Jan. 2008).
Andrew, S. M., et al., "Purification and Fragmentation of Antibodies", *Current Protocols in Immunology*, pp. 2.7.1-2.7.12 (Jan. 1997).
Andrew, S. M., et al., "Fragmentation of Immunoglobulin G", *Current Protocols in Immunology*, pp. 2.8.1-2.8.10 (Jan. 1997).
Arnold, et al., "The Impact of Glycosylation on the Biological Function and Structure of Human Immunoglobulins", *Annu. Rev. Immunol.*, 25(1): 21-50 (Jan. 2007).
Collin, M., et al., "EndoS and SpeB from *Streptococcus pyogenes* Inhibit Immunoglobulin-Mediated Opsonophagocytosis", *Infection and Immunity*, 70(12): 6646-6651 (Dec. 2002).
Collin, M., et al., "EndoS, a novel secreted protein from *Streptococcus pyogenes* with endoglycosidase activity on human IgG", *The EMBO Journal*, 20(12): 3046-3055 (Jun. 2001).
Collin, M., et al., "Effect of SpeB and EndoS from *Streptococcus pyogenes* on Human Immunoglobulins", *Inspection and Immunity*, 69(11): 7187-7189 (Nov. 2001).
Collin, M. et al., "A Novel Secreted Endoglycosidase from *Enterococcus faecalis* with Activity on Human Immunoglobulin G and Ribonuclease B", *The Journal of Biological Chemistry*, 279(21): 22558-22570 (May 2004).
Jones, D.H., et al., "Fc Receptor-mediated Binding and Endocytosis by Human Mononuclear Phagocytes: Monomeric IgG Is Not Endocytosed by U937 Cells and Monocytes", *The Journal of Cell Biology*, 100(2): 558-564 (Feb. 1985).
Kumagai, K., et al., "Studies of Surface Immunoglobulins on Human B Lymphocytes", *The Journal of Immunology*, 115(4): 982-987 (Oct. 1975).
Pettersson, D., et al., "IgG on Human Blood Lymphocytes Studied by Immunofluorescence", *Scand. J. Immunol*, 8(6): 535-542 (Jun. 1978).
Söderberg, J. J., et al., "The *Streptococcal* protease IdeS modulates bacterial IgGFc binding and generates 1/2Fc fragments with the ability to prime polymorphonuclear leucocytes", *Molecular Immunology*, 45(12): 3347-3353 (Jul. 2008).
Notification Concerning Transmittal of International Preliminary Report on Patentability for International Application No. PCT/EP2008/007457 Dated Mar. 25, 2010.

* cited by examiner

*Primary Examiner* — Michail Belyavskyi
(74) *Attorney, Agent, or Firm* — Hamilton, Brook, Smith & Reynolds, P.C.

(57) ABSTRACT

The inventions provides methods and kits for the dissociation of Fcγ-receptor-IgG complexes, and methods and kits for the isolation of IgG and Fc and Fab fragments of IgG.

3 Claims, 9 Drawing Sheets

Table 1. Kinetic constants of EndoS binding immobilized IgG subclasses

| Ig | EndoS (E235Q) | | | EndoS |
|---|---|---|---|---|
| | $ka$ (x $10^4$/M/s) | $kd$ (x $10^{-3}$/s) | KD (x $10^{-7}$M) | |
| IgG1 | 4.2 | 17.6 | 4.2 | nb |
| IgG2 | 1.2 | 2.5 | 2.1 | nb |
| IgG3 | 10.7 | 8.9 | 0.83 | nb |
| IgG4 | 1.5 | 2.0 | 1.4 | nb |
| Deglyc IgG1-4 | nb | nb | nb | nb |

Nb = no binding

Table 2. Kinetic constants of IgG1-IgG4 binding receptor subclasses.

| | FcγRIIa | | | FcγRIIb | | | FcγRIIIa |
|---|---|---|---|---|---|---|---|
| Ig | ka (x 10⁴/M/s) | kd (x 10⁻³/s) | KD (x 10⁻⁷M) | ka (x 10⁴/M/s) | kd (x 10⁻³/s) | KD (x 10⁻⁷ M) | |
| IgG1 | 3.5 | 3.4 | 0.97 | 2.6 | 4.3 | 1.7 | nb |
| IgG2 | nb | nb | nb | nb | nb | nb | nb |
| IgG3 | nb | nb | nb | nb | nb | nb | nb |
| IgG4 | nb | nb | nb | 3.4 | 6.9 | 2.0 | nb |
| Deglyc IgG1-4 | nb | nb | nb | nb | nb | nb | nb |

Nb = no binding

Figure 9

[Sequence alignment figure comparing EndoS-alfa, EndoF2, and CP40 protein sequences from positions 1 to 480]

SEQUENCE LISTING

<160> NUMBER OF SEQ ID NOS: 17

<210> SEQ ID NO 1
<211> LENGTH: 959
<212> TYPE: PRT
<213> ORGANISM: Streptococcus pyogenes

<400> SEQUENCE: 1

Glu Glu Lys Thr Val Gln Val Gln Lys Gly Leu Pro Ser Ile Asp Ser
1               5                   10                  15

Leu His Tyr Leu Ser Glu Asn Ser Lys Lys Glu Phe Lys Glu Glu Leu
            20                  25                  30

Ser Lys Ala Gly Gln Glu Ser Gln Lys Val Lys Glu Ile Leu Ala Lys
        35                  40                  45

Ala Gln Gln Ala Asp Lys Gln Ala Gln Glu Leu Ala Lys Met Lys Ile
    50                  55                  60

Pro Glu Lys Ile Pro Met Lys Pro Leu His Gly Pro Leu Tyr Gly Gly
65                  70                  75                  80

Tyr Phe Arg Thr Trp His Asp Lys Thr Ser Asp Pro Thr Glu Lys Asp
                85                  90                  95

Lys Val Asn Ser Met Gly Glu Leu Pro Lys Glu Val Asp Leu Ala Phe
            100                 105                 110

Ile Phe His Asp Trp Thr Lys Asp Tyr Ser Leu Phe Trp Lys Glu Leu
        115                 120                 125

Ala Thr Lys His Val Pro Lys Leu Asn Lys Gln Gly Thr Arg Val Ile
    130                 135                 140

Arg Thr Ile Pro Trp Arg Phe Leu Ala Gly Gly Asp Asn Ser Gly Ile
145                 150                 155                 160

```
Ala Glu Asp Thr Ser Lys Tyr Pro Asn Thr Pro Gly Asn Lys Ala
            165                 170                 175

Leu Ala Lys Ala Ile Val Asp Glu Tyr Val Lys Tyr Asn Leu Asp
            180                 185                 190

Gly Leu Asp Val Asp Val Glu His Asp Ser Ile Pro Lys Val Asp Lys
            195                 200                 205

Lys Glu Asp Thr Ala Gly Val Glu Arg Ser Ile Gln Val Phe Glu Glu
            210                 215                 220

Ile Gly Lys Leu Ile Gly Pro Lys Gly Val Asp Lys Ser Arg Leu Phe
225                 230                 235                 240

Ile Met Asp Ser Thr Tyr Met Ala Asp Lys Asn Pro Leu Ile Glu Arg
            245                 250                 255

Gly Ala Pro Tyr Ile Asn Leu Leu Val Gln Val Tyr Gly Ser Gln
            260                 265                 270

Gly Glu Lys Gly Gly Trp Glu Pro Val Ser Asn Arg Pro Glu Lys Thr
            275                 280                 285

Met Glu Glu Arg Trp Gln Gly Tyr Ser Lys Tyr Ile Arg Pro Glu Gln
            290                 295                 300

Tyr Met Ile Gly Phe Ser Phe Tyr Glu Glu Asn Ala Gln Glu Gly Asn
305                 310                 315                 320

Leu Trp Tyr Asp Ile Asn Ser Arg Lys Asp Glu Asp Lys Ala Asn Gly
            325                 330                 335

Ile Asn Thr Asp Ile Thr Gly Thr Arg Ala Glu Arg Tyr Ala Arg Trp
            340                 345                 350

Gln Pro Lys Thr Gly Gly Val Lys Gly Gly Ile Phe Ser Tyr Ala Ile
            355                 360                 365

Asp Arg Asp Gly Val Ala His Gln Pro Lys Lys Tyr Ala Lys Gln Lys
            370                 375                 380

Glu Phe Lys Asp Ala Thr Asp Asn Ile Phe His Ser Asp Tyr Ser Val
385                 390                 395                 400

Ser Lys Ala Leu Lys Thr Val Met Leu Lys Asp Lys Ser Tyr Asp Leu
            405                 410                 415

Ile Asp Glu Lys Asp Phe Pro Asp Lys Ala Leu Arg Glu Ala Val Met
            420                 425                 430

Ala Gln Val Gly Thr Arg Lys Gly Asp Leu Glu Arg Phe Asn Gly Thr
            435                 440                 445

Leu Arg Leu Asp Asn Pro Ala Ile Gln Ser Leu Glu Gly Leu Asn Lys
            450                 455                 460

Phe Lys Lys Leu Ala Gln Leu Asp Leu Ile Gly Leu Ser Arg Ile Thr
465                 470                 475                 480

Lys Leu Asp Arg Ser Val Leu Pro Ala Asn Met Lys Pro Gly Lys Asp
            485                 490                 495

Thr Leu Glu Thr Val Leu Glu Thr Tyr Lys Lys Asp Asn Lys Glu Glu
            500                 505                 510

Pro Ala Thr Ile Pro Pro Val Ser Leu Lys Val Ser Gly Leu Thr Gly
            515                 520                 525

Leu Lys Glu Leu Asp Leu Ser Gly Phe Asp Arg Glu Thr Leu Ala Gly
            530                 535                 540

Leu Asp Ala Ala Thr Leu Thr Ser Leu Glu Lys Val Asp Ile Ser Gly
545                 550                 555                 560

Asn Lys Leu Asp Leu Ala Pro Gly Thr Glu Asn Arg Gln Ile Phe Asp
            565                 570                 575
```

```
Thr Met Leu Ser Thr Ile Ser Asn His Val Gly Ser Asn Glu Gln Thr
            580                 585                 590

Val Lys Phe Asp Lys Gln Lys Pro Thr Gly His Tyr Pro Asp Thr Tyr
        595                 600                 605

Gly Lys Thr Ser Leu Arg Leu Pro Val Ala Asn Glu Lys Val Asp Leu
    610                 615                 620

Gln Ser Gln Leu Leu Phe Gly Thr Val Thr Asn Gln Gly Thr Leu Ile
625                 630                 635                 640

Asn Ser Glu Ala Asp Tyr Lys Ala Tyr Gln Asn His Lys Ile Ala Gly
                645                 650                 655

Arg Ser Phe Val Asp Ser Asn Tyr His Tyr Asn Phe Lys Val Ser
            660                 665                 670

Tyr Glu Asn Tyr Thr Val Lys Val Thr Asp Ser Thr Leu Gly Thr Thr
            675                 680                 685

Thr Asp Lys Thr Leu Ala Thr Asp Lys Glu Thr Tyr Lys Val Asp
        690                 695                 700

Phe Phe Ser Pro Ala Asp Lys Thr Lys Ala Val His Thr Ala Lys Val
705                 710                 715                 720

Ile Val Gly Asp Glu Lys Thr Met Met Val Asn Leu Ala Glu Gly Ala
                725                 730                 735

Thr Val Ile Gly Gly Ser Ala Asp Pro Val Asn Ala Arg Lys Val Phe
            740                 745                 750

Asp Gly Gln Leu Gly Ser Glu Thr Asp Asn Ile Ser Leu Gly Trp Asp
            755                 760                 765

Ser Lys Gln Ser Ile Ile Phe Lys Leu Lys Glu Asp Gly Leu Ile Lys
    770                 775                 780

His Trp Arg Phe Phe Asn Asp Ser Ala Arg Asn Pro Glu Thr Thr Asn
785                 790                 795                 800

Lys Pro Ile Gln Glu Ala Ser Leu Gln Ile Phe Asn Ile Lys Asp Tyr
                805                 810                 815

Asn Leu Asp Asn Leu Leu Glu Asn Pro Asn Lys Phe Asp Asp Glu Lys
            820                 825                 830

Tyr Trp Ile Thr Val Asp Thr Tyr Ser Ala Gln Gly Glu Arg Ala Thr
            835                 840                 845

Ala Phe Ser Asn Thr Leu Asn Asn Ile Thr Ser Lys Tyr Trp Arg Val
850                 855                 860

Val Phe Asp Thr Lys Gly Asp Arg Tyr Ser Ser Pro Val Val Pro Glu
865                 870                 875                 880

Leu Gln Ile Leu Gly Tyr Pro Leu Pro Asn Ala Asp Thr Ile Met Lys
                885                 890                 895

Thr Val Thr Thr Ala Lys Glu Leu Ser Gln Lys Asp Lys Phe Ser
            900                 905                 910

Gln Lys Met Leu Asp Glu Leu Lys Ile Lys Glu Met Ala Leu Glu Thr
        915                 920                 925

Ser Leu Asn Ser Lys Ile Phe Asp Val Thr Ala Ile Asn Ala Asn Ala
    930                 935                 940

Gly Val Leu Lys Asp Cys Ile Glu Lys Arg Gln Leu Leu Lys Lys
945                 950                 955
```

<210> SEQ ID NO 2  
<211> LENGTH: 959  
<212> TYPE: PRT  
<213> ORGANISM: Streptococcus pyogenes

```
<400> SEQUENCE: 2

Glu Glu Lys Thr Val Gln Val Gln Lys Gly Leu Pro Ser Ile Asp Ser
1               5                   10                  15

Leu His Tyr Leu Ser Glu Asn Ser Lys Lys Glu Phe Lys Glu Glu Leu
            20                  25                  30

Ser Lys Ala Gly Gln Glu Ser Gln Lys Val Lys Glu Ile Leu Ala Lys
        35                  40                  45

Ala Gln Gln Ala Asp Lys Gln Ala Gln Glu Leu Ala Lys Met Lys Ile
    50                  55                  60

Pro Glu Lys Ile Pro Met Lys Pro Leu His Gly Pro Leu Tyr Gly Gly
65                  70                  75                  80

Tyr Phe Arg Thr Trp His Asp Lys Thr Ser Asp Pro Thr Glu Lys Asp
                85                  90                  95

Lys Val Asn Ser Met Gly Glu Leu Pro Lys Glu Val Asp Leu Ala Phe
            100                 105                 110

Ile Phe His Asp Trp Thr Lys Asp Tyr Ser Leu Phe Trp Lys Glu Leu
        115                 120                 125

Ala Thr Lys His Val Pro Lys Leu Asn Lys Gln Gly Thr Arg Val Ile
    130                 135                 140

Arg Thr Ile Pro Trp Arg Phe Leu Ala Gly Gly Asp Asn Ser Gly Ile
145                 150                 155                 160

Ala Glu Asp Thr Ser Lys Tyr Pro Asn Thr Pro Glu Gly Asn Lys Ala
                165                 170                 175

Leu Ala Lys Ala Ile Val Asp Glu Tyr Val Tyr Lys Tyr Asn Leu Asp
            180                 185                 190

Gly Leu Asp Val Asp Val Gln His Asp Ser Ile Pro Lys Val Asp Lys
        195                 200                 205

Lys Glu Asp Thr Ala Gly Val Glu Arg Ser Ile Gln Val Phe Glu Glu
    210                 215                 220

Ile Gly Lys Leu Ile Gly Pro Lys Gly Val Asp Lys Ser Arg Leu Phe
225                 230                 235                 240

Ile Met Asp Ser Thr Tyr Met Ala Asp Lys Asn Pro Leu Ile Glu Arg
                245                 250                 255

Gly Ala Pro Tyr Ile Asn Leu Leu Leu Val Gln Val Tyr Gly Ser Gln
            260                 265                 270

Gly Glu Lys Gly Gly Trp Glu Pro Val Ser Asn Arg Pro Glu Lys Thr
        275                 280                 285

Met Glu Glu Arg Trp Gln Gly Tyr Ser Lys Tyr Ile Arg Pro Glu Gln
    290                 295                 300

Tyr Met Ile Gly Phe Ser Phe Tyr Glu Glu Asn Ala Gln Glu Gly Asn
305                 310                 315                 320

Leu Trp Tyr Asp Ile Asn Ser Arg Lys Asp Glu Asp Lys Ala Asn Gly
                325                 330                 335

Ile Asn Thr Asp Ile Thr Gly Thr Arg Ala Glu Arg Tyr Ala Arg Trp
            340                 345                 350

Gln Pro Lys Thr Gly Gly Val Lys Gly Gly Ile Phe Ser Tyr Ala Ile
        355                 360                 365

Asp Arg Asp Gly Val Ala His Gln Pro Lys Lys Tyr Ala Lys Gln Lys
    370                 375                 380

Glu Phe Lys Asp Ala Thr Asp Asn Ile Phe His Ser Asp Tyr Ser Val
385                 390                 395                 400

Ser Lys Ala Leu Lys Thr Val Met Leu Lys Asp Lys Ser Tyr Asp Leu
                405                 410                 415
```

-continued

```
Ile Asp Glu Lys Asp Phe Pro Asp Lys Ala Leu Arg Glu Ala Val Met
            420             425             430

Ala Gln Val Gly Thr Arg Lys Gly Asp Leu Glu Arg Phe Asn Gly Thr
        435             440             445

Leu Arg Leu Asp Asn Pro Ala Ile Gln Ser Leu Glu Gly Leu Asn Lys
450             455             460

Phe Lys Lys Leu Ala Gln Leu Asp Leu Ile Gly Leu Ser Arg Ile Thr
465             470             475             480

Lys Leu Asp Arg Ser Val Leu Pro Ala Asn Met Lys Pro Gly Lys Asp
                485             490             495

Thr Leu Glu Thr Val Leu Glu Thr Tyr Lys Lys Asp Asn Lys Glu Glu
            500             505             510

Pro Ala Thr Ile Pro Pro Val Ser Leu Lys Val Ser Gly Leu Thr Gly
        515             520             525

Leu Lys Glu Leu Asp Leu Ser Gly Phe Asp Arg Glu Thr Leu Ala Gly
    530             535             540

Leu Asp Ala Ala Thr Leu Thr Ser Leu Glu Lys Val Asp Ile Ser Gly
545             550             555             560

Asn Lys Leu Asp Leu Ala Pro Gly Thr Glu Asn Arg Gln Ile Phe Asp
                565             570             575

Thr Met Leu Ser Thr Ile Ser Asn His Val Gly Ser Asn Glu Gln Thr
            580             585             590

Val Lys Phe Asp Lys Gln Lys Pro Thr Gly His Tyr Pro Asp Thr Tyr
        595             600             605

Gly Lys Thr Ser Leu Arg Leu Pro Val Ala Asn Glu Lys Val Asp Leu
    610             615             620

Gln Ser Gln Leu Leu Phe Gly Thr Val Thr Asn Gln Gly Thr Leu Ile
625             630             635             640

Asn Ser Glu Ala Asp Tyr Lys Ala Tyr Gln Asn His Lys Ile Ala Gly
                645             650             655

Arg Ser Phe Val Asp Ser Asn Tyr His Tyr Asn Asn Phe Lys Val Ser
            660             665             670

Tyr Glu Asn Tyr Thr Val Lys Val Thr Asp Ser Thr Leu Gly Thr Thr
        675             680             685

Thr Asp Lys Thr Leu Ala Thr Asp Lys Glu Thr Tyr Lys Val Asp
    690             695             700

Phe Phe Ser Pro Ala Asp Lys Thr Lys Ala Val His Thr Ala Lys Val
705             710             715             720

Ile Val Gly Asp Glu Lys Thr Met Met Val Asn Leu Ala Glu Gly Ala
                725             730             735

Thr Val Ile Gly Gly Ser Ala Asp Pro Val Asn Ala Arg Lys Val Phe
            740             745             750

Asp Gly Gln Leu Gly Ser Glu Thr Asp Asn Ile Ser Leu Gly Trp Asp
        755             760             765

Ser Lys Gln Ser Ile Ile Phe Lys Leu Lys Glu Asp Gly Leu Ile Lys
    770             775             780

His Trp Arg Phe Phe Asn Asp Ser Ala Arg Asn Pro Glu Thr Thr Asn
785             790             795             800

Lys Pro Ile Gln Glu Ala Ser Leu Gln Ile Phe Asn Ile Lys Asp Tyr
                805             810             815

Asn Leu Asp Asn Leu Leu Glu Asn Pro Asn Lys Phe Asp Asp Glu Lys
            820             825             830

Tyr Trp Ile Thr Val Asp Thr Tyr Ser Ala Gln Gly Glu Arg Ala Thr
        835             840             845
```

-continued

```
Ala Phe Ser Asn Thr Leu Asn Ile Thr Ser Lys Tyr Trp Arg Val
        850                 855                 860

Val Phe Asp Thr Lys Gly Asp Arg Tyr Ser Ser Pro Val Val Pro Glu
865                 870                 875                 880

Leu Gln Ile Leu Gly Tyr Pro Leu Pro Asn Ala Asp Thr Ile Met Lys
                885                 890                 895

Thr Val Thr Thr Ala Lys Glu Leu Ser Gln Gln Lys Asp Lys Phe Ser
                900                 905                 910

Gln Lys Met Leu Asp Glu Leu Lys Ile Lys Glu Met Ala Leu Glu Thr
                915                 920                 925

Ser Leu Asn Ser Lys Ile Phe Asp Val Thr Ala Ile Asn Ala Asn Ala
                930                 935                 940

Gly Val Leu Lys Asp Cys Ile Glu Lys Arg Gln Leu Leu Lys Lys
945                 950                 955

<210> SEQ ID NO 3
<211> LENGTH: 995
<212> TYPE: PRT
<213> ORGANISM: Streptococcus pyogenes

<400> SEQUENCE: 3

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
                35                  40                  45

Ser Ile Asp Ser Leu His Tyr Leu Ser Glu Asn Ser Lys Lys Glu Phe
            50                  55                  60

Lys Glu Glu Leu Ser Lys Ala Gly Gln Glu Ser Gln Lys Val Lys Glu
65              70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
            115                 120                 125

Thr Glu Lys Asp Lys Val Asn Ser Met Gly Glu Leu Pro Lys Glu Val
130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Thr Ser Lys Tyr Pro Asn Thr Pro Glu
            195                 200                 205

Gly Asn Lys Ala Leu Ala Lys Ala Ile Val Asp Glu Tyr Val Tyr Lys
210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
                260                 265                 270
```

-continued

```
Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
690                 695                 700
```

```
Phe Lys Val Ser Tyr Glu Asn Tyr Thr Val Lys Val Thr Asp Ser Thr
705                 710                 715                 720
Leu Gly Thr Thr Thr Asp Lys Thr Leu Ala Thr Asp Lys Glu Glu Thr
                725                 730                 735
Tyr Lys Val Asp Phe Phe Ser Pro Ala Asp Lys Thr Lys Ala Val His
            740                 745                 750
Thr Ala Lys Val Ile Val Gly Asp Glu Lys Thr Met Met Val Asn Leu
        755                 760                 765
Ala Glu Gly Ala Thr Val Ile Gly Gly Ser Ala Asp Pro Val Asn Ala
    770                 775                 780
Arg Lys Val Phe Asp Gly Gln Leu Gly Ser Glu Thr Asp Asn Ile Ser
785                 790                 795                 800
Leu Gly Trp Asp Ser Lys Gln Ser Ile Ile Phe Lys Leu Lys Glu Asp
                805                 810                 815
Gly Leu Ile Lys His Trp Arg Phe Phe Asn Asp Ser Ala Arg Asn Pro
            820                 825                 830
Glu Thr Thr Asn Lys Pro Ile Gln Glu Ala Ser Leu Gln Ile Phe Asn
        835                 840                 845
Ile Lys Asp Tyr Asn Leu Asp Asn Leu Leu Gly Asn Pro Asn Lys Phe
    850                 855                 860
Asp Asp Glu Lys Tyr Trp Ile Thr Val Asp Thr Tyr Ser Ala Gln Gly
865                 870                 875                 880
Glu Arg Ala Thr Ala Phe Ser Asn Thr Leu Asn Asn Ile Thr Ser Lys
                885                 890                 895
Tyr Trp Arg Val Val Phe Asp Thr Lys Gly Asp Arg Tyr Ser Ser Pro
            900                 905                 910
Val Val Pro Glu Leu Gln Ile Leu Gly Tyr Pro Leu Pro Asn Ala Asp
        915                 920                 925
Thr Ile Met Lys Thr Val Thr Thr Ala Lys Glu Leu Ser Gln Gln Lys
    930                 935                 940
Asp Lys Phe Ser Gln Lys Met Leu Asp Glu Leu Lys Ile Lys Glu Met
945                 950                 955                 960
Ala Leu Glu Thr Ser Leu Asn Ser Lys Ile Phe Asp Val Thr Ala Ile
                965                 970                 975
Asn Ala Asn Ala Gly Val Leu Lys Asp Cys Ile Glu Lys Arg Gln Leu
            980                 985                 990
Leu Lys Lys
        995

<210> SEQ ID NO 4
<211> LENGTH: 3403
<212> TYPE: DNA
<213> ORGANISM: Streptococcus pyogenes

<400> SEQUENCE: 4
ctcttttgtc ctgccatgga tggcaggttg gcaaaaaaat gagaaaagcc taaaaccttt      60
aaatttgtgt tattttacct atactttgta ccttgttttt tttaataaag tgttgttata     120
cttaaggcga actataggaa tgcgcttaca tggatgtgtat atcaactggg aagccatgac     180
ttagtaccaa aaataaggag tgtccaaatg gataaacatt tgttggtaaa agaacacta     240 gggtgtgttt gtgctgcaac gttgatggga gctgccttag cgacccacca tgattcactc     300
aatactgtaa aagcggagga gaagactgtt caggttcaga aaggattacc ttctatcgat     360
agcttgcatt atctgtcaga gaatagcaaa aaagaattta agaagaact ctcaaaagcg     420 gggcaagaat ctcaaaaggt caaagagata ttagcaaaag ctcagcaggc agataaacaa     480
```

```
gctcaagaac ttgccaaaat gaaaattcct gagaaaatac cgatgaaacc gttacatggt    540
cctctctacg gtggttactt tagaacttgg catgacaaaa catcgatcc aacagaaaaa     600
gacaaagtta actcgatggg agagcttcct aaagaagtag atctagcctt tattttccac    660
gattggacaa aagattatag cctttttggg aagaattgg ccaccaaaca tgtgccaaag     720
ttaaacaagc aagggacacg tgtcattcgt accattccat ggcgtttcct agctgggggt    780
gataacagtg gtattgcaga agataccagt aaatacccaa atacaccaga gggaaataaa    840
gctttagcca aagctattgt tgatgaatat gtttataaat acaaccttga tggcttagat    900
gtggatgttg aacatgatag tattccaaaa gttgacaaaa aagaagatac agcaggcgta    960
gaacgctcta ttcaagtgtt tgaagaaatt gggaaattaa ttggaccaaa aggtgttgat   1020
aaatcgcggt tatttattat ggatagcacc tacatggctg ataaaaaccc attgattgag   1080
cgaggagctc cttatattaa tttattactg gtacaggtct atggttcaca aggagagaaa   1140
ggtggttggg agcctgtttc taatcgacct gaaaaaacaa tggaagaacg atggcaaggt   1200
tatagcaagt atattcgtcc tgaacaatac atgattggtt tttctttcta tgaggaaaat   1260
gctcaagaag ggaatctttg gtatgatatt aattctcgca aggacgagga caaagcaaat   1320
ggaattaaca ctgacataac tggaacgcgt gccgaacggt atgcaaggtg caacctaag    1380
acaggtgggg ttaagggagg tatcttctcc tacgctattg accgagatgg tgtagctcat   1440
caacctaaaa aatatgctaa acagaaagag tttaaggacg caactgataa catcttccac   1500
tcagattata gtgtctccaa ggcattaaag acagttatgc taaagataa gtcgtatgat   1560
ctgattgatg agaaagattt cccagataag gctttgcgag aagctgtgat ggcgcaggtt   1620
ggaaccagaa aaggtgattt ggaacgtttc aatggcacat tacgattgga taatccagcg   1680
attcaaagtt tagaaggtct aaataaattt aaaaaattag ctcaattaga cttgattggc   1740
ttatctcgca ttacaaagct cgaccgttct gttttacccg ctaatatgaa gccaggcaaa   1800
gataccttgg aaacagttct tgaaacctat aaaaaggata caaagaaga acctgctact    1860
atcccaccag tatctttgaa ggtttctggt ttaactggtc tgaaagaatt agatttgtca   1920
ggttttgacc gtgaaacctt ggctggtctt gatgccgcta ctctaacgtc tttagaaaaa   1980
gttgatattt ctggcaacaa acttgatttg gctccaggaa cagaaaatcg acaaattttt   2040
gatactatgc tatcaactat cagcaatcat gttggaagca atgaacaaac agtgaaattt   2100
gacaagcaaa aaccaactgg gcattaccca gataccatg ggaaaactag tctgcgctta    2160
ccagtggcaa atgaaaaagt tgatttgcaa agccagcttt tgtttgggac tgtgacaaat   2220
caaggaaccc taatcaatag cgaagcagac tataaggctt accaaaatca taaaattgct   2280
ggacgtagct tgttgattc aaactatcat tacaataact ttaaagtttc ttatgagaac    2340
tataccgtta aagtaactga ttccacattg gaaccacta ctgacaaaac gctagcaact    2400
gataaagaag agacctataa ggttgacttc tttagcccag cagataagac aaaagctgtt   2460
catactgcta aagtgattgt tggtgacgaa aaaaccatga tggttaattt ggcagaaggc   2520
gcaacagtta ttggaggaag tgctgatcct gtaaatgcaa gaaaggtatt tgatgggcaa   2580
ctgggcagtg agactgataa tatctcttta ggatgggatt ctaagcaaag tattatattt   2640
aaattgaaag aagatggatt aataaagcat tggcgtttct tcaatgattc agcccgaaat   2700
cctgagacaa ccaataaacc tattcaggaa gcaagtctac aaattttta atcaaagat     2760
tataatctag ataatttgtt ggaaaatccc aataaatttg atgatgaaaa atattggatt   2820
actgtagata cttacagtgc acaaggagag agagctactg cattcagtaa tacattaaat   2880
```

```
aatattacta gtaaatattg gcgagttgtc tttgatacta aaggagatag atatagttcg    2940
ccagtagtcc ctgaactcca aattttaggt tatccgttac ctaacgccga cactatcatg    3000
aaaacagtaa ctactgctaa agagttatct caacaaaaag ataagttttc tcaaaagatg    3060
cttgatgagt taaaaataaa agagatggct ttagaaactt ctttgaacag taagattttt    3120
gatgtaactg ctattaatgc taatgctgga gttttgaaag attgtattga gaaaaggcag    3180
ctgctaaaaa aataaacaaa gtaacttct tagatagcaa cattcagatt aaattaacaa     3240
aatgtgacta tgataaaggt ttgctggaat tgattaacca aaagactaaa atctgagat    3300 gaatagtccc agattttttag tcttttatag gttttgatga cataaagcta ataatcgtt    3360 agactaccag aaagggcgct tgtccgtgag acatggctgt ctt                      3403
```

<210> SEQ ID NO 5
<211> LENGTH: 24
<212> TYPE: DNA
<213> ORGANISM: Artificial sequence
<220> FEATURE:
<223> OTHER INFORMATION: primer

<400> SEQUENCE: 5
actgggatcc cggaggagaa gact                                           24

<210> SEQ ID NO 6
<211> LENGTH: 24
<212> TYPE: DNA
<213> ORGANISM: Artificial sequence
<220> FEATURE:
<223> OTHER INFORMATION: primer

<400> SEQUENCE: 6
ttaatctcga ggttgctatc taag                                           24

<210> SEQ ID NO 7
<211> LENGTH: 42
<212> TYPE: DNA
<213> ORGANISM: Artificial sequence
<220> FEATURE:
<223> OTHER INFORMATION: primer

<400> SEQUENCE: 7
ccttgatggc ttagatgtgg atgttcaaca tgatagtatt cc                       42

<210> SEQ ID NO 8
<211> LENGTH: 310
<212> TYPE: PRT
<213> ORGANISM: S. Pyogenes

<400> SEQUENCE: 8

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

```
Lys Ile Asn Phe Asn Gly Glu Gln Met Phe Asp Val Lys Glu Ala Ile
                100                 105                 110

Asp Thr Lys Asn His Gln Leu Asp Ser Lys Leu Phe Glu Tyr Phe Lys
            115                 120                 125

Glu Lys Ala Phe Pro Tyr Leu Ser Thr Lys His Leu Gly Val Phe Pro
        130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
290                 295                 300

Ser Trp Asn Gln Thr Asn
305                 310

<210> SEQ ID NO 9
<211> LENGTH: 339
<212> TYPE: PRT
<213> ORGANISM: S. Pyogenes

<400> SEQUENCE: 9

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Pro Ala Asn Phe Thr Gln
50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Lys Gln Lys Ile Asn
        115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160
```

-continued

```
Phe Pro Tyr Leu Ser Thr Lys His Leu Gly Val Phe Pro Asp His Val
            165                 170                 175

Ile Asp Met Phe Ile Asn Gly Tyr Arg Leu Ser Leu Thr Asn His Gly
        180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 10
<211> LENGTH: 1020
<212> TYPE: DNA
<213> ORGANISM: S. Pyogenes

<400> SEQUENCE: 10
atgagaaaaa gatgctattc aacttcagct gcagtattgg cagcagtgac tttatttgtt     60
ctatcggtag atcgtggtgt tatagcagat agttttttctg ctaatcaaga gattagatat    120
tcggaagtaa cacctatca cgttacttcc gtttggacca aggagttac tcctccagca      180 aacttcactc aaggtgaaga tgtttttcac gctccttatg ttgctaacca aggatggtat    240
gatattacca aaacattcaa tggaaaagac gatcttcttt gcggggctgc cacagcaggg    300
aatatgcttc actggtggtt cgatcaaaac aaagaccaaa ttaaacgtta tttggaagag    360
catccagaaa agcaaaaaat aaacttcaat ggcgaacaga tgtttgacgt aaaagaagct    420
atcgacacta aaaccacca gctagatagt aaattatttg aatattttaa agaaaaagct    480
ttcccttatc tatctactaa acacctagga gttttccctg atcatgtaat tgatatgttc    540
attaacggct accgcttag tctaactaac cacggtccaa cgccagtaaa agaaggtagt     600
aaagatcccc gaggtggtat ttttgacgcc gtatttacaa gaggtgatca agtaagcta     660 ttgacaagtc gtcatgattt taagaaaaaa aatctcaaag aaatcagtga tctcattaag    720
aaagagttaa ccgaaggcaa ggctctaggc ctatcacaca cctacgctaa cgtacgcatc    780
aaccatgtta taaacctgtg gggagctgac tttgattcta acgggaacct taaagctatt    840
tatgtaacag actctgatag taatgcatct attggtatga agaaatactt tgttggtgtt    900
aattccgctg gaaaagtagc tatttctgct aagaaaataa agaagataa tattggtgct    960 caagtactag ggttatttac actttcaaca gggcaagata gttggaatca gaccaattaa   1020
```

```
<210> SEQ ID NO 11
<211> LENGTH: 335
<212> TYPE: PRT
<213> ORGANISM: S. Pyogenes

<400> SEQUENCE: 11

Glu Gly Ala Lys Ile Asp Trp Gln Glu Glu Tyr Lys Lys Leu Asp Glu
1               5                   10                  15

Asp Asn Ala Lys Leu Val Glu Val Val Glu Thr Thr Ser Leu Glu Asn
            20                  25                  30

Glu Lys Leu Lys Ser Glu Asn Glu Asn Lys Lys Asn Leu Asp Lys
        35                  40                  45

Leu Ser Lys Glu Asn Gln Gly Lys Leu Glu Lys Leu Glu Leu Asp Tyr
    50                  55                  60

Leu Lys Lys Leu Asp His Glu His Lys Glu His Gln Lys Glu Gln Gln
65                  70                  75                  80

Glu Gln Glu Glu Arg Gln Lys Asn Gln Glu Gln Leu Glu Arg Lys Tyr
                85                  90                  95

Gln Arg Glu Val Glu Lys Arg Tyr Gln Glu Gln Leu Gln Lys Gln Gln
            100                 105                 110

Gln Leu Glu Thr Glu Lys Gln Ile Ser Glu Ala Ser Arg Lys Ser Leu
        115                 120                 125

Ser Arg Asp Leu Glu Ala Ser Arg Ala Ala Lys Lys Asp Leu Glu Ala
    130                 135                 140

Glu His Gln Lys Leu Glu Ala Glu His Gln Lys Leu Lys Glu Asp Lys
145                 150                 155                 160

Gln Ile Ser Asp Ala Ser Arg Gln Gly Leu Ser Arg Asp Leu Glu Ala
                165                 170                 175

Ser Arg Ala Ala Lys Lys Glu Leu Glu Ala Asn His Gln Lys Leu Glu
            180                 185                 190

Ala Glu His Gln Lys Leu Lys Glu Asp Lys Gln Ile Ser Asp Ala Ser
        195                 200                 205

Arg Gln Gly Leu Ser Arg Asp Leu Glu Ala Ser Arg Ala Ala Lys Lys
    210                 215                 220

Glu Leu Glu Ala Asn His Gln Lys Leu Glu Ala Glu Ala Lys Ala Leu
225                 230                 235                 240

Lys Glu Gln Leu Ala Lys Gln Ala Glu Glu Leu Ala Lys Leu Arg Ala
                245                 250                 255

Gly Lys Ala Ser Asp Ser Gln Thr Pro Asp Thr Lys Pro Gly Asn Lys
            260                 265                 270

Ala Val Pro Gly Lys Gly Gln Ala Pro Gln Ala Gly Thr Lys Pro Asn
        275                 280                 285

Gln Asn Lys Ala Pro Met Lys Glu Thr Lys Arg Gln Leu Pro Ser Thr
    290                 295                 300

Gly Glu Thr Ala Asn Pro Phe Phe Thr Ala Ala Leu Thr Val Met
305                 310                 315                 320

Ala Thr Ala Gly Val Ala Ala Val Val Lys Arg Lys Glu Glu Asn
                325                 330                 335

<210> SEQ ID NO 12
<211> LENGTH: 376
<212> TYPE: PRT
<213> ORGANISM: S. Pyogenes
```

<400> SEQUENCE: 12

| | | | | | | | | | | | | | | |
|---|---|---|---|---|---|---|---|---|---|---|---|---|---|---|
| Met | Thr | Arg | Gln | Gln | Thr | Lys | Lys | Asn | Tyr | Ser | Leu | Arg | Lys | Leu | Lys |
| 1 | | | | 5 | | | | | 10 | | | | | 15 | |
| Thr | Gly | Thr | Ala | Ser | Val | Ala | Val | Ala | Leu | Thr | Val | Leu | Gly | Ala | Gly |
| | | | | 20 | | | | | 25 | | | | | 30 | |
| Phe | Ala | Asn | Gln | Thr | Thr | Val | Lys | Ala | Glu | Gly | Ala | Lys | Ile | Asp | Trp |
| | | | | 35 | | | | | 40 | | | | | 45 | |
| Gln | Glu | Glu | Tyr | Lys | Lys | Leu | Asp | Glu | Asp | Asn | Ala | Lys | Leu | Val | Glu |
| | 50 | | | | | 55 | | | | | 60 | | | | |
| Val | Val | Glu | Thr | Thr | Ser | Leu | Glu | Asn | Glu | Lys | Leu | Lys | Ser | Glu | Asn |
| 65 | | | | | 70 | | | | | 75 | | | | | 80 |
| Glu | Glu | Asn | Lys | Lys | Asn | Leu | Asp | Lys | Leu | Ser | Lys | Glu | Asn | Gln | Gly |
| | | | | 85 | | | | | 90 | | | | | 95 | |
| Lys | Leu | Glu | Lys | Leu | Glu | Leu | Asp | Tyr | Leu | Lys | Lys | Leu | Asp | His | Glu |
| | | | | 100 | | | | | 105 | | | | | 110 | |
| His | Lys | Glu | His | Gln | Lys | Glu | Gln | Gln | Glu | Gln | Glu | Arg | Gln | Lys | |
| | | | 115 | | | | | 120 | | | | | 125 | | |
| Asn | Gln | Glu | Gln | Leu | Glu | Arg | Lys | Tyr | Gln | Arg | Glu | Val | Glu | Lys | Arg |
| | 130 | | | | | 135 | | | | | 140 | | | | |
| Tyr | Gln | Glu | Gln | Leu | Gln | Lys | Gln | Gln | Leu | Glu | Thr | Glu | Lys | Gln | |
| 145 | | | | | 150 | | | | | 155 | | | | | 160 |
| Ile | Ser | Glu | Ala | Ser | Arg | Lys | Ser | Leu | Ser | Arg | Asp | Leu | Glu | Ala | Ser |
| | | | | 165 | | | | | 170 | | | | | 175 | |
| Arg | Ala | Ala | Lys | Lys | Asp | Leu | Glu | Ala | Glu | His | Gln | Lys | Leu | Glu | Ala |
| | | | | 180 | | | | | 185 | | | | | 190 | |
| Glu | His | Gln | Lys | Leu | Lys | Glu | Asp | Lys | Gln | Ile | Ser | Asp | Ala | Ser | Arg |
| | | | 195 | | | | | 200 | | | | | 205 | | |
| Gln | Gly | Leu | Ser | Arg | Asp | Leu | Glu | Ala | Ser | Arg | Ala | Ala | Lys | Lys | Glu |
| | 210 | | | | | 215 | | | | | 220 | | | | |
| Leu | Glu | Ala | Asn | His | Gln | Lys | Leu | Glu | Ala | Glu | His | Gln | Lys | Leu | Lys |
| 225 | | | | | 230 | | | | | 235 | | | | | 240 |
| Glu | Asp | Lys | Gln | Ile | Ser | Asp | Ala | Ser | Arg | Gln | Gly | Leu | Ser | Arg | Asp |
| | | | | 245 | | | | | 250 | | | | | 255 | |
| Leu | Glu | Ala | Ser | Arg | Ala | Ala | Lys | Lys | Glu | Leu | Glu | Ala | Asn | His | Gln |
| | | | | 260 | | | | | 265 | | | | | 270 | |
| Lys | Leu | Glu | Ala | Glu | Ala | Lys | Ala | Leu | Lys | Glu | Gln | Leu | Ala | Lys | Gln |
| | | | 275 | | | | | 280 | | | | | 285 | | |
| Ala | Glu | Glu | Leu | Ala | Lys | Leu | Arg | Ala | Gly | Lys | Ala | Ser | Asp | Ser | Gln |
| | 290 | | | | | 295 | | | | | 300 | | | | |
| Thr | Pro | Asp | Thr | Lys | Pro | Gly | Asn | Lys | Ala | Val | Pro | Gly | Lys | Gly | Gln |
| 305 | | | | | 310 | | | | | 315 | | | | | 320 |
| Ala | Pro | Gln | Ala | Gly | Thr | Lys | Pro | Asn | Gln | Asn | Lys | Ala | Pro | Met | Lys |
| | | | | 325 | | | | | 330 | | | | | 335 | |
| Glu | Thr | Lys | Arg | Gln | Leu | Pro | Ser | Thr | Gly | Glu | Thr | Ala | Asn | Pro | Phe |
| | | | 340 | | | | | 345 | | | | | 350 | | |
| Phe | Thr | Ala | Ala | Ala | Leu | Thr | Val | Met | Ala | Thr | Ala | Gly | Val | Ala | Ala |
| | | | | 355 | | | | | 360 | | | | | 365 | |
| Val | Val | Lys | Arg | Lys | Glu | Glu | Asn | | | | | | | | |
| | | | 370 | | | | | 375 | | | | | | | |

<210> SEQ ID NO 13
<211> LENGTH: 1128
<212> TYPE: DNA
<213> ORGANISM: S. pyogenes -continued

```
<400> SEQUENCE: 13
atgactagac aacaaaccaa gaaaaattat tcactacgga aactaaaaac cggtacggct    60
tcagtagccg ttgctttgac cgttttgggc gcaggttttg caaaccaaac aacagttaag   120
gcggaagggg ctaaaattga ttggcaagaa gagtataaaa agttagacga agataatgct   180
aaacttgttg aggttgttga aaccacaagt ttggaaaacg aaaaactcaa gagtgagaat   240
gaggagaata agaaaaattt agacaaactt agcaagaaa atcaaggaaa gctcgaaaaa   300
ttggagcttg actatctcaa aaattagat cacgagcaca agagcacca aaaagaacaa     360 caagaacaag aagagcgaca aaaaaatcaa gaacaattag aacgtaaata ccaacgagaa   420
gtagaaaaac gttatcaaga acaactccaa aaacaacaac aattagaaac agaaaagcaa   480
atctcagaag ctagtcgtaa gagcctaagc cgtgaccttg aagcgtctcg tgcagctaaa   540
aaagaccttg aagctgagca ccaaaaactt gaagctgagc accaaaaact taagaagac    600 aaacaaatct cagacgcaag tcgtcaaggc ctaagccgtg accttgaagc gtctcgtgca   660
gctaaaaaag agcttgaagc aaatcaccaa aaacttgaag ctgagcacca aaaacttaaa   720
gaagacaaac aaatctcaga cgcaagtcgt caaggcctaa gccgtgacct tgaagcgtct   780
cgtgcagcta aaaagagct tgaagcaaat caccaaaaac ttgaagcaga agcaaaagca   840
ctcaaagaac aattagcgaa acaagctgaa gaacttgcaa aactaagagc tggaaaagca   900
tcagactcac aaaccctga tacaaaacca ggaaacaaag ctgttccagg taaaggtcaa   960
gcaccacaag caggtacaaa acctaaccaa aacaaagcac caatgaagga aactaagaga  1020
cagttaccat caacaggtga aacagctaac ccattcttca cagcggcagc ccttactgtt  1080
atggcaacag ctggagtagc agcagttgta aaacgcaaag aagaaaac               1128

<210> SEQ ID NO 14
<211> LENGTH: 37
<212> TYPE: DNA
<213> ORGANISM: Artificial sequence
<220> FEATURE:
<223> OTHER INFORMATION: primer

<400> SEQUENCE: 14
tcggatccgg cgccggaagg ggctaaaatt gattggc                              37

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
ctctgcggcc gctgctgttt cacctgttga aggtaa                               36

<210> SEQ ID NO 16
<211> LENGTH: 26
<212> TYPE: DNA
<213> ORGANISM: Artificial sequence
<220> FEATURE:
<223> OTHER INFORMATION: primer

<400> SEQUENCE: 16
ccggatccgc tagcagatag ttttc                                           26
```

```
<210> SEQ ID NO 17
<211> LENGTH: 26
<212> TYPE: DNA
<213> ORGANISM: Artificial sequence
<220> FEATURE:
<223> OTHER INFORMATION: primer

<400> SEQUENCE: 17
ggcctcgagg gaattggtct gattcc                                              26
```

METHOD OF ASSESSING GLYCOSYLATION STATE OR FUNCTIONAL QUALITY OF AN IGG CONTAINING SAMPLE

This application is the U.S. National Stage of International Application No. PCT/EP2008/007457, filed Sep. 11, 2008, which designates the U.S., published in English, and claims the benefit of U.S. Provisional Application No. 60/960,087, filed Sep. 14, 2007.

INCORPORATION BY REFERENCE OF MATERIAL IN ASCII TEXT FILE

This application incorporates by reference the Sequence Listing contained in the following ASCII text file:
 a) File name: 45951000000Seqlist.txt; created Jun. 21, 2012, 45 KB in size.

FIELD OF THE INVENTION

The present invention relates to isolating a population of cells, to methods for isolating and assessing IgG, to methods for isolating Fab or Fc fragments of IgG, and to kits for carrying out such methods.

BACKGROUND OF THE INVENTION

The immunoglobulin G (IgG) class of antibodies plays an important role in adaptive immune defense of the human host against pathogens. IgG consists of two identical heavy chains and two identical light chains, which in turn are composed of variable and constant domains. Papain treatment of IgG molecule can generate Fab fragments recognizing antigens and Fc fragment, a recognition site for host receptors and a site of interaction with a number of effector molecules.

The Fc portion of IgG also contains a conserved complex carbohydrate or glycan attached to the asparagine 297 residue in the $C_H2$ domain of each heavy chain. These glycans are located in the interface between the $C_H2$ domains when IgG is in its native form. They consist of a biantennary core of N-acetylglucosamine and mannose with added terminal and branching carbohydrate residues such as N-acetylglucosamine, fucose, sialic acid, and galactose. The presence of this carbohydrate is crucial for proper antibody structure and interactions with cellular immunoglobulin G Fcγ receptors (FcγRs) and the complement system.

Endoglycosidase S (EndoS) is secreted by *Streptococcus pyogenes* and has a specific endoglycosidase activity on native IgG by hydrolyzing the conserved glycans attached to the asparagine 297 residue on the heavy chains of IgG. EndoS is the first known bacterial enzyme with a unique specificity for native IgG. In contrast, the activities of other known endoglycosidases require or are enhanced by denaturation of the glycoprotein substrate.

Antibodies such as IgG have many applications in basic research as well as in diagnostics and drug development. In some of these applications, such as immunohistochemistry, immunoassays, tumour detection, radiotherapy, crystallographic studies of antibody binding sites and immunotargeting, it is more convenient to use Fab fragments than whole IgG molecules. Some of the advantages of using Fab fragments are that they will not be affected by Fc receptors on cells or precipitate antigen, they display a reduced immunogenicity and are less susceptible to phagocytosis, and that radiolabelled Fab fragments are more rapidly cleared from tissue than whole IgG molecules. For other applications, it is desirable to use Fc fragments of IgG.

If Fab or Fc fragments are to be produced on a large scale they may be produced as recombinant proteins. For purification purposes, recombinant IgG and serum-produced IgG is often produced as a whole molecule and then chemically processed to obtain Fab or Fc fragments.

The cleavage of IgG into Fab and Fc fragments is most often carried out using proteolytic enzymes such as pepsin or papain. These enzymes often cleave other proteins, so the cleavage reaction generally has to be performed on a purified IgG fraction. Furthermore, pepsin and papain typically cleave IgG in more than one place. This means that the fragments obtained often do not correspond to whole Fab or Fc fragments, and even if cleavage does result in Fab and Fc fragments, they are typically susceptible to further cleavage into smaller fragments. The isolation of Fc fragments from Fab fragments is most often carried out using protein A or G affinity separation columns, which utilise the Fc-binding properties of the bacterial proteins A and G.

SUMMARY OF THE INVENTION

The inventors have made the surprising discovery that contacting cells with EndoS removes IgG which is already bound to FcγRs. In accordance with the present invention, there is thus provided an in vitro method of dissociating Fcγ-receptor-IgG complexes comprising contacting the complexes with an EndoS polypeptide to thereby obtain Fcγ-receptor which is not bound to IgG, wherein optionally the Fcγ-receptor-IgG complexes are present in a cell-containing sample. The invention also provides a method for isolating a population of cells substantially free of Fcγ-receptor-bound IgG molecules, which method comprises:
 (a) contacting a cell-containing sample with an EndoS polypeptide; and
 (b) separating the cells from the contacted sample;
thereby obtaining said population of cells.

The inventors have also identified improved methods for isolating IgG. The methods make use of a modified EndoS polypeptide which lacks endoglycosidase activity. The inventors have shown for the first time that such a modified EndoS polypeptide has unique specificity for the IgG glycoprotein in its native, functionally active form. The method is therefore particularly useful for isolating glycosylated and/or functionally active IgG. By using such a modified EndoS polypeptide in combination with an additional IgG-binding reagent which is capable of binding denatured and/or deglycosylated IgG, the inventors have also identified a method for assessing the glycosylation state or functional quality of an IgG-containing sample.

In accordance with the present invention, there is thus provided a method for isolating IgG from an IgG-containing sample, which method comprises:
 (a) contacting said IgG-containing sample with a modified EndoS polypeptide which lacks IgG endoglycosidase activity
 (b) separating said EndoS from the contacted sample;
thereby obtaining isolated IgG.

Additionally there is provided method of assessing the glycosylation state or functional quality of an IgG-containing sample, which method comprises taking a first and a second sub-sample of the IgG-containing sample, and wherein steps (a) and (b) according to the method above are applied to the first sub-sample, and wherein steps (a) and (b) as above are applied to the second sub-sample except the EndoS polypeptide is substituted with an alternative IgG-binding reagent which is capable of binding denatured and/or deglycosylated IgG, and further comprising:

(c) quantifying the amount of IgG bound to the EndoS polypeptide in the first sub-sample, and the amount of IgG bound to the alternative IgG-binding reagent in the second sub-sample; and (d) comparing both the amounts of bound IgG determined in (c);

and thereby assessing the glycosylation state or functional quality of an IgG containing sample.

The present inventors have also identified improved methods for isolating Fab or Fc fragments of IgG. The methods of the invention make use of a highly specific IgG cleaving enzyme from *S. pyogenes*, IdeS (Immunoglobulin G-degrading enzyme of *S. pyogenes*), and an Fc-binding protein. Accordingly, the methods of the invention do not suffer from the limitations of previous methods as described in the background section, for example those using pepsin and papain. This is because IdeS has only one defined cleavage site within the hinge region of the IgG molecule, and so there is no possibility of further cleavage of the Fab and Fc fragments.

In one method of the invention, a sample containing IgG is contacted with IdeS and an Fc-binding protein. A preferred Fc-binding protein is a modified EndoS polypeptide which lacks endoglycosidase activity as described above. The modified EndoS protein is preferred to widely used alternative Fc-binding proteins, such as protein A and protein G. This is because the modified EndoS protein binds only to Fc, whereas the inventors have found that protein A and protein G may also bind Fab fragments. Therefore it is more difficult to isolate Fab fragments from Fc fragments with these proteins. Other preferred Fc-binding proteins include Protein H.

In the methods of the invention, typically IdeS cleaves the IgG into Fab and Fc fragments and the Fc binding protein binds to the Fc fragments. The Fc fragments are then separated from the Fab fragments.

This method is particularly useful for isolating Fab or Fc fragments from samples comprising purified IgG. More specifically, it is useful for isolating Fab or Fc fragments from a sample comprising IgG purified using the modified EndoS polypeptide of the invention. However, the method can also be adapted for use on samples containing unpurified IgG, such as serum, cell lysate or cell culture medium.

Also provided are kits for carrying out the methods according to the invention and a population of cells isolated by the method according to the invention.

BRIEF DESCRIPTION OF THE FIGURES

FIG. 9 shows a ClustalW amino acid sequence alignment of the EndoS α-domain with EndoF$_2$ from *Elizabethkingia meningoseptica* and CP40 from *Corynebacterium pseudotuberculosis*. Protein names are shown to the left. Amino acid identities and similarities are shown in grey and the consensus sequence is shown under the alignment. The conserved chitinase motif is boxed and the glutamic acid essential for activity is marked with an asterisk below the alignment.

BRIEF DESCRIPTION OF THE SEQUENCES

Figure 1:
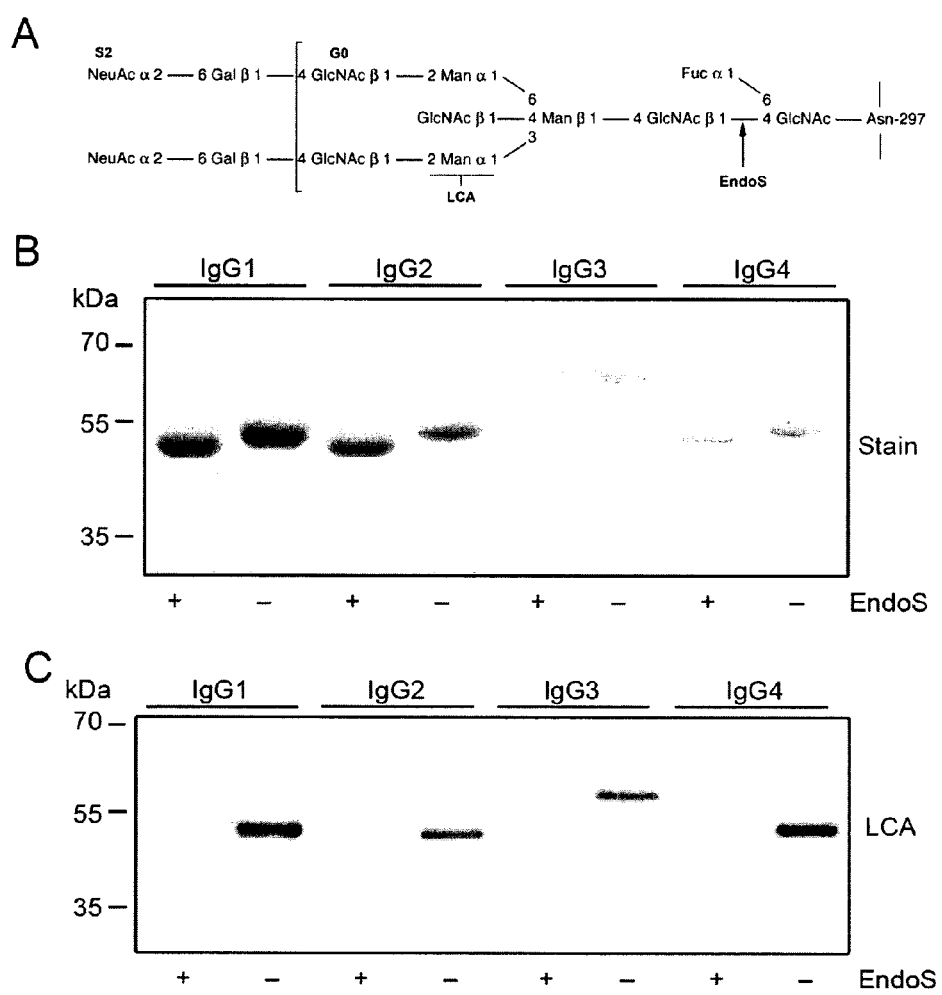
FIG. 1 shows that EndoS has glycosidase activity on all four human IgG subclasses. Panel A: Glycan structure of human IgG. Glycan on the γ-chains of IgG attached to asparagine 297. GlcNAc, N-acetylglucosamine; Fuc, fucose; Man, mannose; Gal, galactose; NeuAc, sialic acid. Cleavage site for EndoS and recognition site for *Lens culinaris* agglutinin lectin (LCA) are indicated. Panel B: Purified $IgG_{1-4}$ incubated with EndoS and analyzed by SDS-PAGE and stained. Panel C: $IgG_{1-4}$ incubated with EndoS and analyzed using LCA lectin blot.

SEQ ID NO: 1 is an amino acid sequence of an EndoS polypeptide isolated from *S. pyogenes* AP1.

SEQ ID NO: 2 is an amino acid sequence of a modified EndoS polypeptide (E235Q) derived from the sequence of SEQ ID NO: 1.

SEQ ID NO: 3 is an amino acid sequence of an EndoS polypeptide isolated from *S. pyogenes* AP1, including a signal sequence. This sequence corresponds to NCBI Accession No: AAK00850.

SEQ ID NO: 4 is a nucleic acid sequence encoding EndoS isolated from *S. pyogenes* AP1, including a signal sequence.

SEQ ID NOS: 5 to 7 are primer sequences.

SEQ ID NO: 8 is an amino acid sequence of IdeS isolated from *S. pyogenes* AP1.

SEQ ID NO: 9 is an amino acid sequence of IdeS isolated from *S. pyogenes* AP1, including a putative signal sequence.

SEQ ID NO: 10 is a nucleic acid sequence encoding IdeS isolated from *S. pyogenes* AP1, including a signal sequence.

SEQ ID NO: 11 is an amino acid sequence of mature protein H.

SEQ ID NO: 12 is an amino acid sequence of protein H, including a signal sequence.

SEQ ID NO: 13 is a nucleic acid sequence encoding protein H, including a signal sequence.

DETAILED DESCRIPTION OF THE INVENTION

General Polypeptide Features

The present invention provides various methods which utilize the bacterial proteins EndoS and IdeS, as well as other proteins. The terms protein, peptide and polypeptide are used interchangeably herein. It will be understood that certain methods of the invention require an EndoS polypeptide having IgG endoglycosidase activity, whereas other methods of the invention require a modified EndoS polypeptide lacking said activity.

The following section relates to general features of all polypeptides of the invention, and in particular to variations, alterations, modifications or derivatisations of amino acid sequence which are included within the polypeptides of the invention. It will be understood that such variations, alterations, modifications or derivatisations of polypeptides as are described herein are subject to the requirement that the polypeptides retain any further required activity or characteristic as may be specified subsequent sections of this disclosure.

Variants of polypeptides of the invention may be defined by particular levels of amino acid identity which are described in more detail in subsequent sections of this disclosure. Amino acid identity may be calculated using any suitable algorithm. For example the PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate homology (for example used on its default settings) (Devereux et al (1984) *Nucleic Acids Research* 12, 387-395).

It will be understood that variants of polypeptides of the invention also includes substitution variants. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |

-continued

| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

The polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

The amino acid sequence of polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

Polypeptides for use in the invention may also be produced using D-amino acids. In such cases the amino acids will be linked in reverse sequence in the C to N orientation. This is conventional in the art for producing such polypeptides. A number of side chain modifications are known in the art and may be made to the side chains of the polypeptides, subject to the polypeptides retaining any further required activity or characteristic as may be specified herein.

It will also be understood that the polypeptides used in the invention may be chemically modified, e.g. post-translationally modified. For example, they may be glycosylated, phosphorylated or comprise modified amino acid residues. They may be modified by the addition of a signal sequence to promote insertion into the cell membrane.

The polypeptides of the invention may also be derivatised or modified to assist with their isolation or purification. Thus, in one embodiment of the invention, the polypeptide for use in the invention is derivatised or modified by addition of a ligand which is capable of binding directly and specifically to a separation means. Alternatively, the polypeptide is derivatised or modified by addition of one member of a binding pair and the separation means comprises a reagent that is derivatised or modified by addition of the other member of a binding pair. Any suitable binding pair can be used. In a preferred embodiment where the polypeptide for use in the invention is derivatised or modified by addition of one member of a binding pair, the polypeptide is preferably histidine-tagged or biotin-tagged. Typically the amino acid coding sequence of the histidine or biotin tag is included at the gene level and the proteins are expressed recombinantly in E. coli. The histidine or biotin tag is typically present at one end of the polypeptide, either at the N-terminus or at the C-terminus. The histidine tag typically consists of six histidine residues, although it can be longer than this, typically up to 7, 8, 9, 10 or 20 amino acids or shorter, for example 5, 4, 3, 2 or 1 amino acids. Furthermore, the histidine tag may contain one or more amino acid substitutions, preferably conservative substitutions as defined above.

EndoS Polypeptides Having IgG Endoglycosidase Activity

Figure 8:
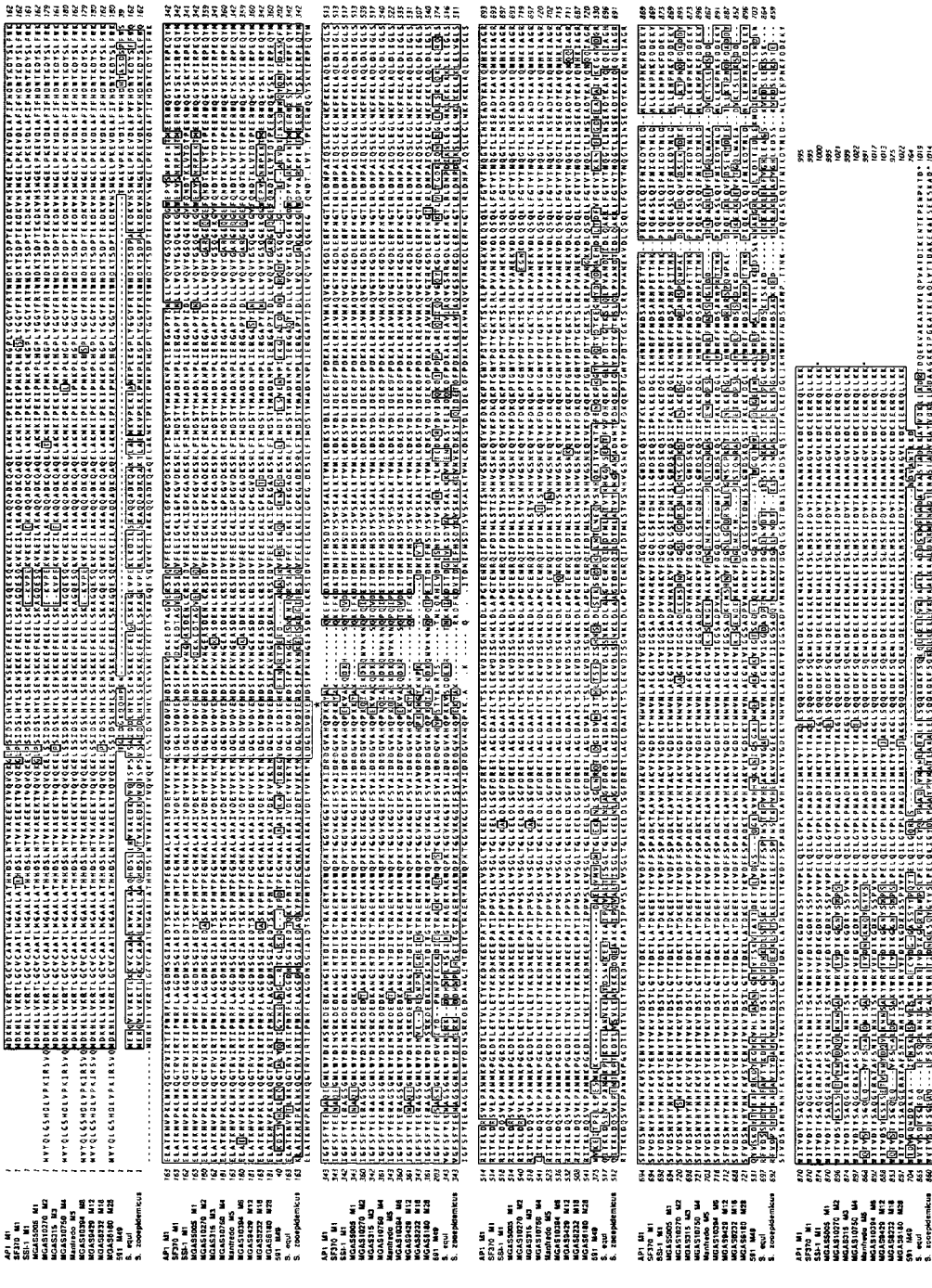
FIG. 8 shows a ClustalW amino acid sequence alignment of EndoS homologues from different *S. pyogenes* serotypes, *S. equi* and *S. zooepidemicus*. Strain names, species, and M serotypes are shown to the left. Amino acid identities and similarities are shown in grey and the consensus sequence is shown under the alignment. The conserved chitinase motif is boxed and the glutamic acid essential for activity is marked with an asterisk below the alignment.
Figure 9:
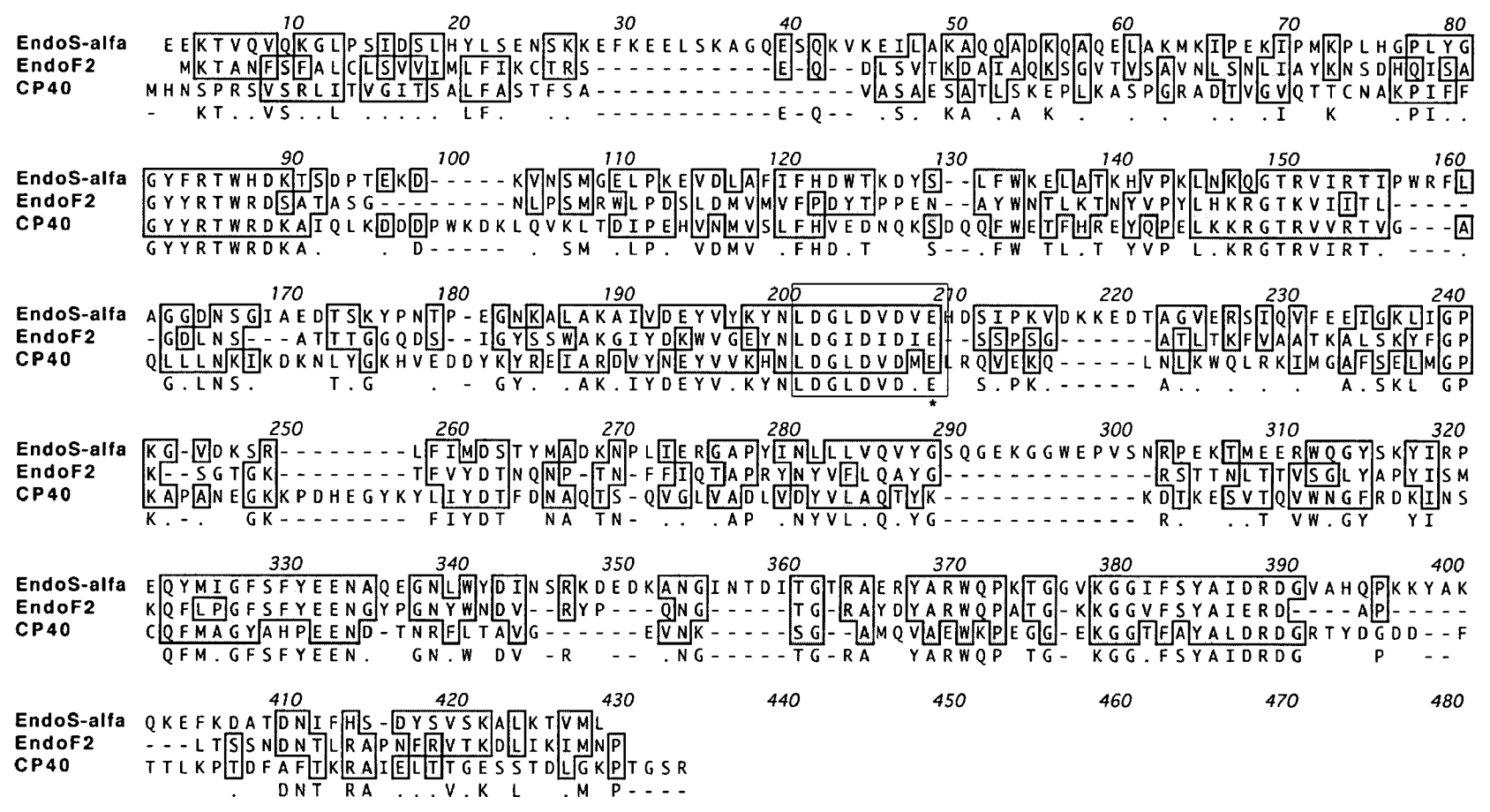

The EndoS polypeptide in this instance is preferably S. pyogenes EndoS, or a variant or fragment of S. pyogenes EndoS which retains IgG endoglycosidase activity. The variant may be an EndoS polypeptide from another organism, such as another bacterium. The bacterium is preferably a Streptococcus, such as Streptococcus equi, Streptococcus zooepidemicus or, preferably, Streptococcus pyogenes. Alternatively, the variant may be from Corynebacterium pseudotuberculosis, for example the CP40 protein; Enterococcus faecalis, for example the EndoE protein; or Elizabethkingia meningoseptica (formerly Flavobacterium meningosepticum), for example the EndoF2 protein. The sequences of EndoS variants from various S. pyogenes serotypes and from S. equi and S. zooepidemicus are shown in FIG. 8. FIG. 9 shows an alignment of the α-domain of EndoS with EndoF2 from Elizabethkingia meningoseptica and CP40 from Corynebacterium pseudotuberculosis.

The EndoS polypeptide may comprise:
(a) the amino acid sequence of SEQ ID NO: 1;
(b) a variant thereof having at least 50% identity to the amino acid sequence of SEQ ID NO: 1 and having IgG endoglycosidase activity; or
(c) a fragment of either thereof having IgG endoglycosidase activity.

Preferably, the polypeptide comprises, or consists of, the sequence of SEQ ID NO: 1. SEQ ID NO: 1 is the sequence of the mature form of EndoS from S. pyogenes, without the signal sequence. The EndoS polypeptide of the invention may additionally comprise a signal sequence. For example, the EndoS polypeptide of the invention may comprise the amino acid sequence of the immature form of EndoS from S. pyogenes, which is publicly available (NCBI Accession No: AAK00850) and is provided as SEQ ID NO: 3. SEQ ID NO: 1 corresponds to amino acids 37 to 995 of SEQ ID NO: 3.

Variant polypeptides as described in this section are those for which the amino acid sequence varies from that in SEQ ID NO: 1 or 3, but which retain the IgG endoglycosidase activity of EndoS. Such variants may include allelic variants and the deletion, modification or addition of single amino acids or groups of amino acids within the protein sequence, as long as the peptide maintains IgG endoglycosidase activity.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made, provided the modified polypeptide retains activity as an IgG-specific endoglycosidase.

Variants of the amino acid sequence of SEQ ID NO: 1 or 3 preferably contain residues 191 to 199 of SEQ ID NO: 1, i.e. Leu-191, Asp-192, Gly-193, Leu-194, Asp-195, Val-196, Asp-197, Val-198 and Glu-199 of SEQ ID NO: 1 (residues 227 to 235 of SEQ ID NO: 3, i.e. Leu-227, Asp-228, Gly-229, Leu-230, Asp-231, Val-232, Asp-233, Val-234 and Glu-235 of SEQ ID NO: 3). These amino acids constitute a chitinase family 18 active site, ending with glutamic acid. The glutamic acid in the active site of chitinases is essential for enzymatic activity. Most preferably, therefore, the variant of SEQ ID NO: 1 or 3 contains glutamic acid at the position equivalent to position 199 of SEQ ID NO: 1 (position 235 of SEQ ID NO: 3). The variant of SEQ ID NO: 1 may contain residues 191 to 199 of SEQ ID NO: 1 (227 to 235 of SEQ ID NO: 3) having one or more conservative substitutions, provided that the variant contains glutamic acid at the position equivalent to position 199 of SEQ ID NO: 1 (position 235 of SEQ ID NO: 3).

Typically, polypeptides which display the IgG endoglycosidase activity of EndoS with more than about 50%, 55% or 65% identity, preferably at least 70%, at least 80%, at least 90% and particularly preferably at least 95%, at least 97% or at least 99% identity, with the amino acid sequence of SEQ ID NO: 1 or 3 are considered variants of the protein The identity of variants of SEQ ID NO: 1 or 3 may be measured over a region of at least 100, at least 250, at least 500, at least 750, at least 800, at least 850, at least 900, at least 950, at least 955 or more contiguous amino acids of the sequence shown in SEQ ID NO: 1, or more preferably over the full length of SEQ ID NO: 1 or 3.

The fragment of the EndoS polypeptide used in the invention is typically at least 10, for example at least 20, 30, 40, 50 or more amino acids in length, up to 100, 200, 250, 300, 500, 750, 800, 850, 900, 950 or 955 amino acids in length, as long as it retains the IgG endoglycosidase activity of EndoS. Preferably, the fragment of the EndoS polypeptide used in the invention encompasses residues 191 to 199 of SEQ ID NO: 1, i.e. Leu-191, Asp-192, Gly-193, Leu-194, Asp-195, Val-196, Asp-197, Val-198 and Glu-199 of SEQ ID NO: 1 (residues 227 to 235 of SEQ ID NO: 3, i.e. Leu-227, Asp-228, Gly-229, Leu-230, Asp-231, Val-232, Asp-233, Val-234 and Glu-235 of SEQ ID NO: 3). A preferred fragment of the invention consists of amino acids 1 to 409 of SEQ ID NO: 1 (amino acids 37 to 445 of SEQ ID NO: 3), which corresponds to the enzymatically active α-domain of EndoS generated by cleavage by the streptococcal cysteine proteinase SpeB. Another preferred fragment consists of amino acids 37 to 995 of SEQ ID NO: 3, which corresponds to the secreted form of EndoS after removal of the signal sequence.

Polypeptides for use in the present invention may be isolated from any suitable organism that expresses an EndoS polypeptide or a variant of an EndoS polypeptide. Typically, the EndoS polypeptide is isolated from suitable EndoS expressing strains of *Streptococcus*, preferably strains of *S. pyogenes*. Suitable organisms and strains may be identified by a number of techniques. For example, *S. pyogenes* strains may initially be tested for the presence an ndoS gene. Polynucleotide primers or probes may be designed based on, for example, SEQ ID NOs: 1 or 3. The presence of the ndoS gene can then be verified by PCR using such primers or by hybridisation of probes to genomic DNA of the *S. pyogenes* strain.

Streptococcal strains expressing active EndoS or a variant thereof can be identified by assaying for IgG endoglycosidase activity in the culture supernatant or by immunodetection using antibodies directed towards EndoS. The Streptococcal strains that have been verified as expressing active EndoS are the *S. pyogenes* M1 serotype strains AP1 and SF370, the *S. equi* strain 4047 and the *S. zooepidermicus* strain H70. In addition, the ndoS gene is found in the following *S. pyogenes* strains: M1 serotype strains SSI-1 and MGAS5005, M2 serotype strain MGAS10270, M3 serotype strain MGAS315, M4 serotype strain MGAS 10750, M5 serotype strain Manfredo, M6 serotype strain MGAS10394, M12 serotype strain MGAS9429, M18 serotype strain MGAS8232, M28 serotype strain MGAS6180 and M49 serotype strain 591.

Isolation and purification of EndoS from an expressing *S. pyogenes* culture, or from cultures of other cells expressing EndoS is typically on the basis of IgG endoglycosidase activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for IgG endoglycosidase activity and peak activity fractions may be pooled. Fractions may be analysed by SDS PAGE. Fractions may be stored at −80° C. In an alternative method to purify EndoS, EndoS without the signal sequence (i.e. having the sequence of SEQ ID NO: 1) is expressed in *Escherichia coli* using GST Gene Fusion System (Amersham-Pharmacia Biotech, Uppsala, Sweden). A 2929 base pair PCR product covering bases 304 to 3232 of the ndoS sequence is amplified from *S. pyogenes* genomic DNA using primers 5'-ACT-GGG-ATC-CCG-GAG-GAG-AAG-ACT-3' (SEQ ID NO: 5) with a BamHI site (underlined) and 5'-TTA-ATC-TCG-AGG-TTG-CTA-TCT-AAG-3' (SEQ ID NO: 6) with an XhoI site (underlined). This fragment is digested with BamHI and XhoI and ligated into the pGEX-5X-3 generating plasmid pGEXndoS that is used to transform *E. coli* BL21 (DE3)pLys. pGEXndoS/BL21(DE3)pLys is induced with 0.1 mM isopropyl β-D-thiogalactopyranoside. After induction, bacteria are lysed using BugBuster™ (Novagen) and the GST-EndoS fusion protein is purified on Glutathione-Sepharose®. The GST tag is removed using factor Xa according to protocols (Amersham-Pharmacia Biotech), and residual factor Xa is removed using Xarrest™-agarose (Novagen). This results in a preparation of recombinant EndoS (rEndoS) that is homogenous as assessed by SDS-PAGE and Western blot using EndoS-specific antibodies. Prior to in vivo experiments protein samples are sterile-filtered through a 0.2 μm filter (Millipore). Purified EndoS protein is stored at −80° C. in phosphate buffered saline.

Polypeptides for use in the invention may also be prepared as fragments of such isolated polypeptides. Further, the EndoS polypeptides may also be made synthetically or by recombinant means. For example, a recombinant EndoS polypeptide may be produced by transfecting mammalian cells in culture with an expression vector comprising a nucleotide sequence encoding the polypeptide operably linked to suitable control sequences, culturing the cells, extracting and purifying the EndoS polypeptide produced by the cells.

The EndoS polypeptides of invention described in this section display IgG endoglycosidase activity. Preferably, the polypeptide hydrolyses IgG or IgG Fc fragments by hydrolysing the conserved glycan linked to the asparagine residue corresponding to residue 297 of a full-length IgG heavy chain polypeptide. Preferably, the polypeptide hydrolyzes the β-1,4-di-N-acetylchitobiose core of the asparagine-linked glycan. Preferably the activity is specific for IgG.

The endoglycosidase activity may be determined by means of a suitable assay. For example, a test polypeptide may be incubated with IgG at a suitable temperature, such as 37° C. The starting materials and the reaction products may then be analysed by SDS PAGE. Typically, the molecular mass of the IgG heavy chain is reduced by approximately 3 kDa if the test polypeptide has IgG endoglycosidase activity. Another assay for determining whether a test polypeptide has IgG endoglycosidase activity is by detection of glycosylated IgG using *Lens culinaris* agglutinin lectin (LCA), optionally using horseradish peroxidase and peroxidase substrate. Typically, the carbohydrate signal is reduced if the test polypeptide has IgG endoglycosidase activity. Another assay for determining whether a test polypeptide has IgG endoglycosidase activity is by incubation of a test polypeptide with purified IgG Fc fragments followed by reduction of the sample with 10 mM dithiotreitol and mass spectroscopy (MALDI-TOF) analysis.

Typically, the mass of monomeric IgG Fc is reduced by 1417±14 Da if the test polypeptide has IgG endoglycosidase activity.

The endoglycosidase activity of the polypeptides can be further characterised by inhibition studies.

The endoglycosidase activity of the polypeptide is generally IgG-specific in that the polypeptide may not degrade the other classes of Ig, namely IgM, IgA, IgD and IgE, when incubated with these immunoglobulins under conditions that permit cleavage of IgG. The EndoS polypeptide is capable of hydrolyzing IgG molecules present in a sample taken from a subject. Thus, where the subject is a human, the EndoS polypeptide is capable of hydrolyzing the glycans on the heavy chains of human IgG. EndoS is capable of hydrolyzing human IgG of all four subclasses ($IgG_{1-4}$). In preferred embodiments, the EndoS polypeptide has the ability to hydrolyze human, Rhesus monkey, mouse, rat, rabbit, horse, goat, dog and swine IgG.

EndoS Polypeptides which Lack IgG Endoglycosidase Activity

The EndoS polypeptide in this instance is preferably modified S. pyogenes EndoS, which has been engineered to lack IgG endoglycosidase activity but which possesses IgG binding activity. By IgG binding activity it will be understood that the modified EndoS binds to IgG, or a variant or fragment thereof, in particular the Fc fragment thereof, which is normally glycosylated. By "normally glycosylated" it will be understood that the IgG molecule, or variant of fragment thereof, is a glycoprotein comprising at least the IgG polypeptide heavy chain (or variant of fragment thereof) coupled to at least one carbohydrate group as found coupled to naturally occurring IgG molecules. In particular, the at least one carbohydrate group is a glycan linked to the asparagine residue corresponding to residue 297 of a full-length IgG heavy chain polypeptide. Preferably, the asparagine-linked glycan has a β-1,4-di-N-acetylchitobiose core.

The EndoS polypeptide is preferably engineered by site-directed mutagenesis. By IgG binding activity it will be understood that the EndoS polypeptides described in this section bind at least one, preferably two, three or all four of the IgG subclasses, $IgG_{1-4}$. Preferably the at least one IgG subclass is bound with high affinity and/or high specificity.

By high affinity it is meant that the binding affinity constant ($K_D$) for the interaction of the modified EndoS with an IgG subclass is greater than 0.05 µM, preferably greater than 0.06 µM, 0.07 µM or 0.08 µM. Binding activity may be determined, and binding affinity may be assessed by any suitable means. For example, by surface plasmon resonance interaction analysis, equilibrium dialysis analysis, or any standard biochemical methods in conjunction with, for example, Scatchard analysis.

By high specificity, it is meant that the polypeptide may not bind the other classes of Ig, namely IgM, IgA, IgD and IgE, when incubated with these immunoglobulins under conditions that permit binding to IgG.

The variant may be derived from an EndoS polypeptide from another organism, such as another bacterium, as is described in the preceding section with the exception that the variant in this instance lacks IgG endoglycosidase activity but possesses IgG binding activity. The modified EndoS polypeptide may comprise:

(a) the amino acid sequence of SEQ ID NO: 2;
(b) a variant thereof having at least 50% identity to the amino acid sequence of SEQ ID NO: 2 which lacks IgG endoglycosidase activity; or
(c) a fragment of either thereof which lacks IgG endoglycosidase activity. Preferably, the polypeptide comprises, or consists of, the sequence of SEQ ID NO: 2. SEQ ID NO: 2 is derived from the sequence of SEQ ID NO: 1, but has been engineered to lack IgG endoglycosidase activity by the substitution of glutamic acid (E) for glutamine (Q) at position 199 of SEQ ID NO: 1. This corresponds to position 235 of SEQ ID NO: 3 (NCBI Accession No: AAK00850) and this particular modification is referred to as E235Q. Such polypeptides typically possess IgG-binding activity as described above.

Variant polypeptides as described in this section are those for which the amino acid sequence varies from that in SEQ ID NO: 2, but which lack IgG endoglycosidase activity and retain IgG-binding activity. Such variants may include allelic variants and the deletion, modification or addition of single amino acids or groups of amino acids within the protein sequence, as long as the peptide maintains the above characteristics.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made, provided the modified polypeptide lacks IgG endoglycosidase activity and retains IgG-binding activity.

Variants of the amino acid sequence of SEQ ID NO: 2 preferably contain residues 191 to 199 of SEQ ID NO: 2, i.e. Leu-191, Asp-192, Gly-193, Leu-194, Asp-195, Val-196, Asp-197, Val-198 and Gln-199 of SEQ ID NO: 2 (equivalent to residues 191 to 199 of SEQ ID NO: 1). These amino acids constitute a chitinase family 18 active site as in SEQ ID NO: 1, except the C terminal glutamic acid is replaced with glutamine. The glutamic acid in the active site of chitinases is essential for enzymatic activity. Most preferably, therefore, the variant of SEQ ID NO: 2 contains glutamine at the position equivalent to position 199 of SEQ ID NO: 2. The variant of SEQ ID NO: 2 may contain residues 191 to 199 of SEQ ID NO: 2 having one or more conservative substitutions, provided that the variant does not contain glutaminic acid at the position equivalent to position 199 of SEQ ID NO: 2.

Typically, polypeptides which lack IgG endoglycosidase activity and retain IgG-binding activity with more than about 50%, 55% or 65% identity, preferably at least 70%, at least 80%, at least 90% and particularly preferably at least 95%, at least 97% or at least 99% identity, with the amino acid sequence of SEQ ID NO: 2 are considered variants of the protein The identity of variants of SEQ ID NO: 2 may be measured over a region of at least 100, at least 250, at least 500, at least 750, at least 800, at least 850, at least 900, at least 950, at least 955 or more contiguous amino acids of the sequence shown in SEQ ID NO: 2, or more preferably over the full length of SEQ ID NO: 2.

The fragment of the EndoS polypeptide used in the invention is typically at least 10, for example at least 20, 30, 40, 50 or more amino acids in length, up to 100, 200, 250, 300, 500, 750, 800, 850, 900, 950 or 955 amino acids in length, as long as it lacks IgG endoglycosidase activity and retains IgG-binding activity. Preferably, the fragment of the EndoS polypeptide used in the invention in this instance encompasses residues 191 to 199 of SEQ ID NO: 2, i.e. Leu-191, Asp-192, Gly-193, Leu-194, Asp-195, Val-196, Asp-197, Val-198 and Gln-199 of SEQ ID NO: 2. A preferred fragment of the invention consists of amino acids 1 to 409 of SEQ ID NO: 2 (amino which corresponds to the enzymatically active α-domain of EndoS generated by cleavage by the streptococcal cysteine proteinase SpeB.

Streptococcal strains expressing an EndoS or a variant thereof that lacks IgG endoglycosidase activity and retains IgG-binding activity can be identified by immunodetection using antibodies directed towards EndoS, followed by assaying for IgG endoglycosidase activity and IgG-binding activity as described above. The Streptococcal strains that have been verified as expressing active EndoS are described in the above section. These strains represent good candidates for the possible expression of EndoS polypeptides that lack IgG endoglycosidase activity and retain IgG-binding activity. Isolation and purification of EndoS from an expressing *S. pyogenes* culture is also described above.

In an alternative method, an EndoS protein with the desired characteristics can be produced by altering a nucleotide encoding an EndoS protein, and then expressing said nucleotide in a suitable system. Suitable methods include site-directed mutagenesis of the nucleotide encoding the protein. This technique has been widely used in the study of protein functions. The technique is typically oligonucleotide-based and involves the following steps:

(1) Cloning the DNA encoding the protein of interest into a plasmid vector.

(2) Denaturing the plasmid DNA to produce single strands.

(3) Contacting the denatured DNA with a synthetic oligonucleotide (or oligonucleotides) complementary to the target sequence but incorporating the desired mutation(s) (point mutation, deletion, or insertion), such that the synthetic oligonucleotide anneals to the target region.

(4) Extending the mutated strand by a DNA-polymerase using the plasmid DNA strand as the template.

(5) Propagating the heteroduplex (mutated/non-mutated strand) by transformation in *E. coli*.

After propagation, about 50% of the produced heteroduplexes are mutants and the other 50% are "wild type" (no mutation). Selection and enrichment methods are used to favor the production of mutants. For example, the parental non-mutated strand can be digested with a restriction enzyme that only digests methylated DNA (DpnI). This allows removal of the parental strand from the reaction before transformation of *E. coli* by since the newly synthesized strands are un-methylated while the parental strand (if purified from the correct *E. coli* background) is methylated.

Alternatives to site-directed mutagenesis include:

(1) Polymerase chain reaction (PCR) based methods using specific mutagenic primers, or error-prone PCR with subsequent screening for desired mutations or loss/gain of protein function.

(2) Introduction of a plasmid harboring the gene of interest into an *E. coli* mutator strain (deficient in DNA proofreading systems) and subsequent screening for desired mutations or loss/gain of protein function.

(3) Chemical synthesis of partial or whole genes containing the desired mutations and subsequent introduction into an appropriate protein expression system.

Alternatively, an EndoS protein with the desired characteristics can be produced by DNA-independent methods, which include chemical synthesis of parts of a polypeptide with the desired mutation.

Polypeptides for use in the invention may also be prepared as fragments of such isolated polypeptides. Further, the EndoS polypeptides may also be made synthetically or by recombinant means. For example, a recombinant EndoS polypeptide may be produced by transfecting mammalian cells in culture with an expression vector comprising a nucleotide sequence encoding the polypeptide operably linked to suitable control sequences, culturing the cells, extracting and purifying the EndoS polypeptide produced by the cells.

The IgG binding activity of the polypeptide is generally IgG-specific in that the polypeptide may not bind the other classes of Ig, namely IgM, IgA, IgD and IgE, when incubated with these immunoglobulins under conditions that permit binding interactions. The EndoS polypeptide is capable of binding to IgG molecules present in a sample taken from a subject. Thus, where the subject is a human, the EndoS polypeptide is capable of binding human IgG. EndoS is capable of binding human IgG of all four subclasses ($IgG_{1-4}$). In preferred embodiments, the EndoS polypeptide has the ability to bind human, Rhesus monkey, mouse, rat, rabbit, horse, goat, dog and swine IgG.

IdeS

IdeS is an extracellular cysteine protease produced by the human pathogen *S. pyogenes* and is described in WO 03/051914. IdeS was originally isolated from a group A streptococcal strain of serotype M1, but the ides gene has now been identified in all tested group A streptococcal strains. IdeS has an extraordinarily high degree of substrate specificity, with its only identified substrate being IgG. IdeS catalyses a single proteolytic cleavage in the lower hinge region of human IgG. This proteolytic degradation promotes inhibition of opsonophagocytosis and interferes with the killing of group A *Streptococcus*. IdeS also cleaves some subclasses of IgG in various animals and efficiently converts IgG into Fc and Fab fragments. The ides gene has been cloned and expressed in *E. coli* as a GST fusion protein.

The IdeS polypeptide for use in the methods of the invention is preferably *S. pyogenes* IdeS, or a variant or fragment of *S. pyogenes* IdeS which retains cysteine protease activity. The variant may be an IdeS polypeptide from another organism, such as another bacterium. The bacterium is preferably a *Streptococcus*. The *Streptococcus* is preferably a group A *Streptococcus*, a group C *Streptococcus* or a group G *Streptococcus*. In particular, the variant may be an IdeS polypeptide from a group C *Streptococcus* such as *S. equii* or *S. zooepidemicus*. Alternatively, the variant may be from *Pseudomonas putida*.

The IdeS polypeptide may comprise:

(a) the amino acid sequence of SEQ ID NO: 8;

(b) a variant thereof having at least 50% identity to the amino acid sequence of SEQ ID NO: 8 and having IgG cysteine protease activity; or (c) a fragment of either thereof having IgG cysteine protease activity.

Preferably, the IdeS polypeptide comprises, or consists of, the sequence of SEQ ID NO: 8. SEQ ID NO: 8 is the sequence of the mature form of IdeS, without the signal sequence, and corresponds to amino acids 30 to 339 of SEQ ID NO: 9.

Variant IdeS polypeptides are those for which the amino acid sequence varies from that in SEQ ID NO: 8, but which display the same IgG cysteine protease activity as IdeS. Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 8 are considered variants of the protein. Such variants may include allelic variants and the deletion, modification or addition of single amino acids or groups of amino acids within the protein sequence, as long as the peptide maintains the basic functionality of IdeS. The identity of variants of SEQ ID NO: 8 may be measured over a region of at least 50, at least 75, at least 100, at least 150, at least 200, at least 250, at least 275, at least 300 or more contiguous amino acids of the sequence shown in SEQ ID NO: 8, or more preferably over the full length of SEQ ID NO: 8.

Variants of the amino acid sequence of SEQ ID NO: 8 preferably contain residues Lys-55 and/or Cys-65 and/or His-233 and/or Asp-255 and/or Asp-257 of SEQ ID NO: 8. Most preferably, the variant of SEQ ID NO: 8 contains each of residues Lys-55, Cys-65, His-233, Asp-255 and Asp-257 of SEQ ID NO: 8.

The variant sequences typically differ by at least 1, 2, 5, 10, 20, 30, 50 or more mutations (which may be substitutions, deletions or insertions of amino acids). For example, from 1 to 50, 2 to 30, 3 to 20 or 5 to 10 amino acid substitutions, deletions or insertions may be made. The modified polypeptide retains activity as an IgG-specific cysteine protease. Preferably the variant polypeptides comprise a cysteine residue and a histidine residue at a spacing typically found in cysteine proteases. For example, in SEQ ID NO: 8, these residues are found at a spacing of about 130 amino acids, as is typically found in cysteine proteases.

The fragment of the IdeS polypeptide used in the invention is typically at least 10, for example at least 15, 20, 25, 30, 40, 50 or more amino acids in length, up to 100, 150, 200, 250 or 300 amino acids in length, as long as it retains the IgG cysteine protease activity of IdeS. Preferably, the fragment of the IdeS polypeptide used in the invention encompasses residues Lys-55 and/or Cys-65 and/or His-233 and/or Asp-255 and/or Asp-257 of SEQ ID NO: 1. Most preferably, the fragment encompasses each of residues Lys-55, Cys-65, His-233, Asp-255 and Asp-257 of SEQ ID NO: 8.

IdeS polypeptides for use in accordance with the invention display immunoglobulin cysteine protease activity, and in particular IgG cysteine protease activity. Preferably, the polypeptide cleaves IgG in the hinge region and more particularly in the hinge region of the heavy chain. Cleavage results in production of Fc and Fab fragments of IgG. Preferably the activity is specific for IgG. The cysteine protease activity may be determined by means of a suitable assay. For example, a test polypeptide may be incubated with IgG at a suitable temperature, such as 37° C. The starting materials and the reaction products may then be analysed by SDS PAGE to determine whether the desired IgG cleavage product is present. Typically this cleavage product is a 31 kDa fragment. Typically there is no further degradation of IgG after this first cleavage. The cleavage product may be subjected to N-terminal sequencing to verify that cleavage has occurred in the hinge region of IgG. Preferably the N-terminal sequence comprises the sequence GPSVFLFP.

The cysteine protease activity of the polypeptides can be further characterised by inhibition studies. Preferably, the activity is inhibited by the peptide derivate Z-LVG-CHN$_2$ and/or by iodoacetic acid both of which are protease inhibitors. However, the activity is generally not inhibited by E64.

The cysteine protease activity of the polypeptides is generally IgG-specific in that the polypeptides may not degrade the other classes of Ig, namely IgM, IgA, IgD and IgE, when incubated with these immunoglobulins under conditions that permit cleavage of IgG. The IdeS polypeptide is capable of cleaving human IgG. In preferred embodiments the polypeptide has the ability to cleave human, rabbit, mouse or goat IgG.

IdeS polypeptides for use in the present invention may be isolated from any suitable organism that expresses an IdeS polypeptide. Typically, the IdeS polypeptide is isolated from suitable IdeS expressing strains of *S. pyogenes*. Suitable organisms and strains may be identified by a number of techniques. For example, *S. pyogenes* strains may initially be tested for the presence an ides gene. Polynucleotide primers or probes may be designed based on for example, SEQ ID NOs: 8, 9 or 10. The presence of the ides gene can then be verified by PCR using the primers or by hybridisation of the probes to genomic DNA of the *S. pyogenes* strain.

*S. pyogenes* strains expressing active IdeS can be identified by assaying for IgG cysteine protease activity in the culture supernatant. Preferably inhibitor E64 is added to the supernatant to inhibit any SpeB cysteine protease activity. At least five strains express active IdeS: strains AP1, AP12, AP55, KTL3 and SF370. Preferably the expressing strain is selected from AP1, AP12 and AP55.

Isolation and purification of IdeS from an expressing *S. pyogenes* culture, or from cultures of other cells expressing IdeS is typically on the basis of IgG cysteine protease activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for IgG cysteine protease activity and peak activity fractions may be pooled. Fractions may be analysed by SDS PAGE. For example, an N-terminal sequence can be obtained from the SDS PAGE protein band. Fractions may be stored at −20° C.

Fc Binding Proteins

A preferred Fc-binding protein for use in the methods of the invention is a modified EndoS polypeptide which lacks endoglycosidase activity as described in the relevant section of the description above. The modified EndoS polypeptide of the invention binds Fc fragments of all IgG subclasses, provided they are normally glycosylated.

Another preferred Fc binding protein for use in the methods of the invention is Protein H. Protein H is expressed by *S. pyogenes* and is described in EP-A-0371199 and WO 91/19740. Protein H has a characteristic spectrum of immunoglobulin-binding properties, for example binding to the Fc part of IgG. It is also capable of binding albumin. A number of regions within protein H have been identified, and designated as the S, A, B, C1, C2, C3 and D regions. The IgG Fc-binding domains reside in the AB region, whilst the C-repeats (C1, C2 and C3) are responsible for albumin binding. Protein H has also been found to target to the nucleus and have cytostatic effects.

The protein H polypeptide for use in the methods of the invention is preferably *S. pyogenes* protein H, or a variant or fragment of *S. pyogenes* protein H which retains IgG Fc-binding activity. The variant may be a protein H polypeptide from another organism, such as another bacterium. The bacterium is preferably a *Streptococcus*.

The protein H polypeptide may comprise:
(a) the amino acid sequence of SEQ ID NO: 11;
(b) a variant thereof having at least 50% identity to the amino acid sequence of SEQ ID NO: 11 and having IgG Fc-binding activity; or
(c) a fragment of either thereof having IgG Fc-binding activity.

Preferably, the protein H polypeptide comprises, or consists of, the sequence of SEQ ID NO: 11. SEQ ID NO: 11 is the sequence of the mature form of protein H, without the signal sequence, and corresponds to amino acids 42 to 376 of SEQ ID NO: 12.

Variant polypeptides are those for which the amino acid sequence varies from that in SEQ ID NO: 11, but which display the same IgG Fc-binding activity as protein H. Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 11 are considered variants of the protein. Such variants may include allelic variants and the deletion, modification or addition of single amino acids or groups of amino acids within the protein sequence, as long as the peptide maintains the basic functionality of protein H. The identity of variants of SEQ ID NO: 11 may be measured over a region of at least 50, at least 75, at least 100, at least 150, at least 200, at least 250, at least 275, at least 300 or more contiguous amino acids of the sequence shown in SEQ ID NO: 11 or more preferably over the full length of SEQ ID NO: 11.

Variants of the amino acid sequence of SEQ ID NO: 4 preferably contain amino acids 1 to 117 of SEQ ID NO: 11, which is the N-terminal AB region of protein H that contains the residues responsible for IgG Fc-binding. Such variants most preferably contain residues 84 to 108 of SEQ ID NO: 11, which is part of the IgG Fc-binding region of protein H. Variants of protein H preferably contain the C repeats (C1, C2 and C3) of protein H, i.e. amino acids 118 to 242 of SEQ ID NO: 11.

The variant sequences typically differ by at least 1, 2, 5, 10, 20, 30, 50 or more mutations (which may be substitutions, deletions or insertions of amino acids). For example, from 1 to 50, 2 to 30, 3 to 20 or 5 to 10 amino acid substitutions, deletions or insertions may be made. The modified polypeptide retains IgG Fc-binding activity.

The fragment of the protein H polypeptide used in the invention is typically at least 10, for example at least 15, 20, 25, 30, 40, 50 or more amino acids in length, up to 100, 150, 200, 250, 300 or 325 amino acids in length, as long as it retains the IgG Fc-binding activity of protein H. Preferably, the fragment of the protein H polypeptide used in the invention encompasses residues 84 to 108 of SEQ ID NO: 11. Preferred fragments of SEQ ID NO: 11 include: amino acids 1 to 117 of SEQ ID NO: 11, which is the N-terminal AB region of protein H and contains the region responsible for IgG Fc-binding; amino acids 1 to 108 of SEQ ID NO: 11; amino acids 1 to 80 of SEQ ID NO: 11, which is the N-terminal A region; amino acids 1 to 77 of SEQ ID NO: 11; amino acids 81 to 117 of SEQ ID NO: 11, which is the B region of protein H; amino acids 1 to 305 of SEQ ID NO: 11, which is the form of protein H produced recombinantly in $E.$ $coli$; and amino acids 1 to 285 of SEQ ID NO: 11, which is the form of protein H cleaved from the Streptococcal cell surface by the action of a streptococcal cysteine protease.

Polypeptides for use in accordance with the invention display IgG Fc-binding activity. IgG Fc-binding activity may be determined by means of a suitable assay, such as Western blot or slot blot analysis using radiolabelled IgG Fc as a probe or by means of ELISA, for example as described in Frick et al. (1994), Molecular Microbiology 12:143-151.

The IgG Fc-binding activity of the protein H polypeptides can be further characterised by inhibition studies. For example, binding of radiolabelled protein H to IgG Fc immobilized on polyacrylamide beads can be inhibited with protein H polypeptides, for example as described in Frick et al. (1994), Molecular Microbiology 12:143-151.

The Fc-binding activity of the protein H polypeptides is generally IgG-specific in that the polypeptides may not bind to the other classes of Ig, namely IgM, IgA, IgD and IgE, when incubated with these immunoglobulins under conditions that permit binding to IgG. The protein H polypeptide is capable of binding to human IgG. In preferred embodiments the polypeptide has the ability to bind human, rabbit and baboon IgG.

Protein H polypeptides for use in the present invention may be isolated from any suitable organism that expresses protein H. Typically, the protein H polypeptide is isolated from suitable protein H expressing strains of $S.$ $pyogenes$. Suitable organisms and strains may be identified by a number of techniques. For example, $S.$ $pyogenes$ strains may initially be tested for the presence of a gene encoding protein H. Polynucleotide primers or probes may be designed based on, for example, SEQ ID NOs: 11, 12 or 13. The presence of the gene encoding protein H can then be verified by PCR using the primers or by hybridisation of the probes to genomic DNA of the $S.$ $pyogenes$ strain.

$S.$ $pyogenes$ strains expressing active protein H can be identified by assaying for IgG binding activity in the culture supernatant. The strains of $S.$ $pyogenes$ expressing active protein H are strains belonging to the M1 serotype, such as AP1.

Isolation and purification of a protein H from an expressing $S.$ $pyogenes$ culture, or from cultures of other cells expressing protein H is typically on the basis of IgG binding activity. Preferably the purification method involves an affinity chromatography step using IgG coupled to sepharose.

Similar considerations to the above apply to other suitable Fc binding proteins which may be used in the methods of the invention. For example, one or more of Protein G (typically derived from Streptococcal bacteria), Protein A (typically derived from Staphylococcal bacteria) and Protein A/G (a recombinant fusion protein that combines IgG binding domains of both Protein A and Protein G) may be used instead of or in addition to Protein H in the methods of the invention. These proteins are well-characterised as native and recombinant proteins of microbial origin which all possess the ability to bind to the Fc region of mammalian immunoglobulins. The interaction between the various proteins and immunoglobulins is not equivalent for all antibody subclasses and it will be understood that Fc binding proteins with IgG-specific Fc binding activity are preferred.

Method for Isolating a Population of Cells which are Substantially Free of IgG Molecules Bound to FcγRs.

IgGs, classified in four subclasses, $IgG_1$, $IgG_2$, $IgG_3$ and $IgG_4$, are described to interact with different types of FcγRs giving different activation profiles. FcγRs provide a linkage between the humoral and cellular immune responses. Phagocytic cells express members of three classes of IgG-Fc receptors, FcγRI, FcγRII and FcγRIII, characterized by structural and functional homology and specific recognition site on the $C_H2$ region of IgG. Binding of pathogen-IgG complexes to FcγRs mediates an essential response from host against pathogens by initiating a cascade of signals causing antibody-dependent-cellular-cytotoxicity (ADCC), complement-dependent-cellular-cytotoxicity (CDCC), endocytosis, phagocytosis, oxidative burst, release of inflammatory mediators, etc. Complexed IgG-FcγR can besides activation of the C1q component of complement also activate other ligands e.g. mannan binding lectin (MBL), the neonatal receptor FcRn, the mannose receptor (MR), etc. FcγRs may be expressed constitutively on haematopoietic cells and may be induced or up-regulated by cytokines and other agents. FcγRs are responsible for balancing activation (FcγRI, FcγRIIa and FcγRIIIa) and inhibitory signals (FcγRIIb) in the immune system with the ability to both activate and inhibit IgG mediated effector stimulation.

The effects mediated by FcγRs are therefore of great interest in the study of immunology. However, evaluation of such effects is complicated in vitro because cells isolated from subjects or individuals are typically pre-loaded with IgG bound to their FcγRs. Accordingly the receptors are blocked, preventing further analysis. No suitable reagent exists in the art to strip bound IgG from FcγRs without producing additional damage to cells. Researchers have thus been obliged to use cell lines expressing FcγRs which can be cultured in the absence of IgG. This provides only an approximation of native cells isolated from a subject, and accordingly research in this area has been hindered. The present inventors have demonstrated that EndoS polypeptides having IgG endoglycosidase activity can hydrolyse all subclasses of IgG, preventing their binding to FcγRs. Furthermore, the inventors have demonstrated that contacting cells with EndoS leads to the release of bound IgG from the FcγRs. Therefore, studies that previously have been limited to cells lines can now be performed on native cells. This will, for example, allow studies of IgG/receptor affinities, kinetics, and calculations of number of receptors per cell, and elucidate Fc-mediated signaling events in native cells rather than cell lines.

The present invention therefore provides methods for isolating a population of cells substantially free of Fcγ-receptor-bound IgG molecules, which method comprises contacting a cell-containing sample with an EndoS polypeptide and separating the cells from the contacted sample, thereby obtaining said population of cells.

The cell-containing sample may be a blood or serum sample taken from a subject or individual, or may be cell culture medium. The subject or individual is preferably a human but may be an animal, preferably selected from Rhesus monkey, mouse, rat, rabbit, horse, goat, dog and swine.

The cell-containing sample is contacted with EndoS polypeptide under conditions suitable for interaction between the polypeptide and the cells to take place and endoglycosidase activity to occur. Suitable conditions include use of EndoS at a concentration of at least 1 µg/ml, 2 µg/ml, 4 µg/ml, 6 µg/ml, 8 µg/ml, 10 µg/ml, 12 µg/ml, 15 µg/ml or 20 µg/ml, preferably at least 10 µg/ml. Suitable conditions also include incubation of the cell-containing sample with EndoS for at least 20 minutes, 30 minutes, 40 minutes, 50 minutes, 60 minutes, 70 minutes, 80 minutes, 90 minutes or 120 minutes, preferably at least 90 minutes. Incubation preferably takes place at room temperature, more preferably at approximately 20° C., 25° C., 30° C., 35° C., 40° C. or 45° C., and most preferably at approximately 37° C.

Cells are separated from the contacted sample by any suitable means. Suitable means include those which result in the separation of viable cells. These means therefore include methods which do not damage the cells or induce inflammatory responses in the cells. Suitable means include, for example, gentle washing of the cells. By gentle washing it is intended to encompass at least one instance of centrifugation of the cell-containing sample at approximately 1000×g for approximately 5 minutes, followed by aspiration of the supernatant and resuspension of the pellet in suitable fresh cell culture medium. The centrifugation, aspiration and resuspension steps are preferably repeated at least one, two, three, four, or preferably five times.

Alternative means may comprise methods for the removal of the EndoS polypeptide from the sample, or methods for the removal of the cleaved IgG from the sample. A preferred method for removal of the EndoS from a sample comprises using an EndoS which is derivatised or modified as described above.

A preferred modification comprises the addition of a histidine tag. The presence of a histidine tag means that the polypeptide binds with a high affinity to a reagent or separating means containing chelating groups on its surface which carry a nickel, copper or zinc ion. The histidine tag binds strongly to these metal ions. Such a reagent can therefore be used to separate EndoS from a sample.

Another preferred modification comprises the addition of a biotin tag. The presence of a biotin tag means that the polypeptide binds with a high affinity to a reagent or separating means comprising streptavidin. The biotin tag binds strongly to streptavidin. Such a reagent can therefore be used to separate EndoS from a sample.

Preferred reagents or separating means are populations of magnetic particles capable of binding to the EndoS polypeptide. For example, where the EndoS polypeptide is derivatised with a histidine tag, the magnetic particles contain on their surface chelating groups which carry a nickel, copper or zinc ion. Alternatively, where the EndoS polypeptide is derivatised with a biotin tag, the magnetic particles contain on their surface streptavidin.

Accordingly, a preferred method of removing EndoS from a sample comprises using a population of magnetic particles as described above and carrying out magnetic field separation on the sample. The magnetic particles are preferably magnetic nanoparticles, and the magnetic field separation is preferably high-gradient magnetic field separation.

It will be understood that any suitable separation means may be used. For example, ultracentrifugation and ultrasound based separation technologies may be used. As a further example, in one embodiment, the separation means comprises a solid support. Preferred solid supports include cross-linked agarose beads, or similar, which may be used as the matrix in an affinity chromatography column. Alternatively the solid support may comprise a suitable silica-based material or polystyrene. In one embodiment the solid support may comprise a plastic container such as a microtiter plate or equivalent, to which the polypeptide to be separated can be directly adsorbed.

Alternative separation means include reagents comprising antibodies specific to the polypeptide to be separated, which may be generated by methods standard in the art. Antibodies in this sense include a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, F(ab')2 or Fv fragment. If more than one antibody is present, the antibodies preferably have different non-overlapping determinants such that they may bind to the polypeptide simultaneously. The antibody may be bound to a solid support or may be labeled or conjugated to another chemical group or molecule to assist with their separation or isolation. For example, typical chemical groups include fluorescent labels such as Fluorescein (FITC) or Phycoerythrin (PE), or tags such as biotin.

Further alternative means may additionally comprise methods for the removal of the IgG which has been dissociated from Fcγ-receptors. The dissociated IgG could be removed from the sample by the addition of an alternative IgG binding reagent which is capable of binding IgG in an unglycosylated and/or denatured form. Suitable agents include Protein A and Protein G. These agents could then be separated from from the sample, thereby removing the dissociated IgG. The alternative IgG binding reagents may be derivatised or modified as described above for EndoS to assist with their separation. A preferred alternative IgG binding reagent would be derivatised or modified to interact with the same separation means as the derivatised or modified EndoS described above. For example, the alternative IgG binding agent could be derivatised or modified to interact with the same population of magnetic particles as the derivatised or modified EndoS. Both the EndoS polypeptide and the alternative IgG binding agent may then be removed from the sample by magnetic field separation.

Method for Determining the Presence or Absence of IgG in a Sample, or for Isolating IgG from an IgG-Containing Sample The isolation and/or detection of IgG is typically carried out in the art using such agents as Protein G or Protein A. These bacterial proteins interact well with IgG. However, Protein A does not bind to all four IgG subclasses ($IgG_{1-4}$), and both Protein A and Protein G are unable to discriminate between unglycosylated and/or denatured, inactive IgG and glycosylated and/or native, functionally active IgG. By contrast, the present inventors have identified that EndoS polypeptides which lack IgG endoglycosidase activity typically bind all four IgG subclasses with high affinity, and are selective for normally glycosylated IgG, i.e. IgG in its native, functionally active form.

Accordingly, the present invention provides an improved method for determining the presence or absence of IgG in a sample, which method comprises contacting said sample with an EndoS polypeptide which lacks IgG endoglycosidase activity, separating said EndoS from the contacted sample, and thereby determining the presence or absence of IgG and, optionally, where IgG is present, obtaining isolated IgG. The invention therefore also provides a method for isolating IgG from an IgG-containing sample, which method comprises contacting said sample with an EndoS polypeptide which lacks IgG endoglycosidase activity, separating said EndoS from the contacted sample, and thereby obtaining isolated IgG.

The above samples are contacted with EndoS polypeptide under conditions suitable for interaction between the polypeptide and the sample to take place and IgG binding activity to occur, i.e. to allow formation of a IgG-EndoS polypeptide complex. Suitable conditions include use of EndoS at a concentration of at least 1 µg/ml, 2 µg/ml, 4 µg/ml, 6 µg/ml, 8 µg/ml, 10 µg/ml, 12 µg/ml, 15 µg/ml or 20 µg/ml, preferably at least 10 µg/ml. Suitable conditions also include incubation of the sample with EndoS for at least 20 minutes, 30 minutes, 40 minutes, 50 minutes, 60 minutes, 70 minutes, 80 minutes, 90 minutes or 120 minutes, preferably at least 60 minutes. Incubation preferably takes place at room temperature, more preferably at approximately 20° C., 25° C., 30° C., 35° C., 40° C. or 45° C., and most preferably at approximately 37° C.

A particular advantage of EndoS in these methods is that EndoS specifically binds to normally glycosylated IgG. The IgG binding activities of other IgG binding agents typically require or are enhanced by denaturation of the IgG glycoprotein. This is typically achieved by treating an IgG-containing sample with acid. Such treatment may damage or denature some antibodies (acid-sensitive antibodies). Since the method of the invention requires no such treatment, the method is particularly suitable for isolating acid-sensitive IgG in its native form from a sample.

The EndoS may separated from the contacted sample by any suitable method. A preferred method for removal of the EndoS from a sample comprises using an EndoS which is derivatised or modified as described above.

A preferred modification comprises the addition of a histidine tag. The presence of a histidine tag means that the polypeptide binds with a high affinity to a reagent or separating means containing chelating groups on its surface which carry a nickel, copper or zinc ion. The histidine tag binds strongly to these metal ions. Such a reagent can therefore be used to separate EndoS from a sample.

Another preferred modification comprises the addition of a biotin tag. The presence of a biotin tag means that the polypeptide binds with a high affinity to a reagent or separating means comprising streptavidin. The biotin tag binds strongly to streptavidin. Such a reagent can therefore be used to separate EndoS from a sample.

Preferred reagents or separating means are populations of magnetic particles capable of binding to the EndoS polypeptide. For example, where the EndoS polypeptide is derivatised with a histidine tag, the magnetic particles contain on their surface chelating groups which carry a nickel, copper or zinc ion. Alternatively, where the EndoS polypeptide is derivatised with a biotin tag, the magnetic particles contain on their surface streptavidin.

Accordingly, a preferred method of removing EndoS from a sample comprises using a population of magnetic particles as described above and carrying out magnetic field separation on the sample. The magnetic particles are preferably magnetic nanoparticles, and the magnetic field separation is preferably high-gradient magnetic field separation.

It will be understood that any suitable separation means may be used. For example, the alternative means described in the preceding section.

The EndoS of the contacted sample may be assessed for the presence or absence of bound IgG by any suitable means.

For example, the molecular weight of the EndoS may be analysed. EndoS bound to IgG will have a higher molecular weight than EndoS not bound to IgG. Accordingly suitable methods include any method able to discriminate protein species by weight, for example SDS-PAGE and Western Blot, Mass spectrometry etc. Alternatively, the above Western Blot may be directly analysed for the presence of IgG by using IgG-specific antibodies or antibodies specific to a particular IgG sub-class. Detection of proteins in a blot in this manner is a widely used technique in the art.

Other suitable means for detecting the presence or absence of IgG bound to EndoS include incubating the EndoS with antibodies to IgG or IgG-binding proteins with coupled enzymes (e.g. horseradish peroxidase, alkaline phosphatase) followed by addition of fluorogenic/chromogenic substrates. In this instance, the development of a colour signal indicates the presence of IgG, with the quantity of IgG being proportional to the strength of the signal. Detection of proteins in this manner is a widely used technique in the art.

Further suitable means for detecting the presence or absence of IgG bound to EndoS comprise first separating bound IgG from EndoS so that it can be analysed/detected independently of EndoS by any of the above methods or any suitable method. IgG may be separated from EndoS by any suitable means. Suitable means include the elution of IgG from EndoS by contacting the EndoS from the contacted sample with a suitable elution buffer. The choice of elution buffer will typically depend on whether or not the IgG bound to EndoS is known or suspected to be acid-sensitive, i.e. denatured/inactivated by contact with acids.

Where the antibody is not acid-sensitive, an elution protocol using a low pH elution buffer may typically be employed. Elution protocols of this type are well known in the art. Such elution buffers have a pH typically below about pH 3, most preferably below about pH 2. Preferred examples include 0.1 M Glycine at pH2. In addition, or optionally, such elution buffers may typically comprise at least one of the following:

Sodium or potassium salts, preferably at a concentration of about 0.5M to about 1M;

Mono-, di-, or polysaccharides with structures similar to the glycan associated with Asn-297 on native IgG;

or any combination thereof

However, as outlined above, the methods of the invention are particularly suitable for detection/isolation of acid-sensitive antibodies. Where the IgG bound to EndoS is known or suspected to be acid-sensitive, it is therefore preferable to use elution buffers and protocols which do not require a low pH. Such protocols are also known in the art and are based on the principle of providing a buffer comprising a molecule which competes with the bound IgG for binding to EndoS, thus leading to release of the bound IgG. Suitable competition elution buffers therefore typically comprise one or more mono-, di-, or polysaccharides with structures similar to the glycan associated with Asn-297 on native IgG. Particularly preferred elution buffers comprise sucrose at about 0.25M to about 0.5M, preferably with pH from about 5.3 to about 8.3. Examples of specific preferred elution buffers include, for example: Sucrose 0.25M, in PBS pH7.4; Sucrose 0.5M, in PBS pH7.4; Sucrose 0.25M, in PBS pH5.3; Sucrose 0.25M, in PBS pH8.5 and Sucrose 0.25M, Maltose 0.25M, in PBS pH7.4.

In addition, or optionally, such competition elution buffers may typically comprise Sodium or potassium salts, preferably at a concentration of about 0.5M to about 1M.

The means for separating bound IgG from EndoS as described above may also be used to obtain isolated IgG.

Method of Assessing the Glycosylation State and/or Functional Quality of an IgG Containing Sample As described above, the EndoS polypeptides of the invention lacking IgG endoglycosidase activity and having IgG binding activity are specific for glycosylated and/or native, functionally active IgG. Therefore, by using said EndoS polypeptides in combination with an alternative IgG-binding reagent, the present invention provides a method of assessing the glycosylation state or functional quality of an IgG containing sample, which method comprises taking a first and a second sub-sample from the IgG-containing sample, contacting the first sub-sample with an EndoS polypeptide as described in the preceding section and the second sub-sample with an alternative IgG-binding reagent which is capable of binding unglycosylated and/or denatured, inactive IgG, and then quantifying the amount of IgG bound to the EndoS polypeptide in the first sub-sample, and the amount of IgG bound to the alternative IgG-binding reagent in the second sub-sample. Finally, by comparing both of the amounts of bound IgG determined in the first and second sub-samples, the glycosylation state or functional quality of an IgG containing sample can be assessed.

The alternative IgG-binding reagent is typically Protein A or Protein G, which bind to all forms (native or denatured) of IgG. In this instance, the amount of IgG bound to said reagent therefore represents the total IgG present in the second sub-sample. The EndoS polypeptide binds only to glycosylated and/or native, functionally active IgG, and therefore the amount of IgG bound to EndoS represents only the glycosylated and/or native, functionally active IgG present in the first sub-sample. By comparing the concentration of total IgG from the second sub-sample to the concentration of native IgG in the first sample, the skilled person will recognise that one obtains a ratio which reflects the proportion of IgG in the original sample which is present in its glycosylated and/or native, functionally active form.

In another embodiment, the alternative IgG-binding reagent could be specific for unglycosylated and/or denatured IgG. Such a reagent could be, for example, an antibody. Accordingly, in this embodiment the proportion of IgG in the original sample which is present in its glycosylated and/or native, functionally active form can be assessed by the formula:

Amount of IgG in first sub-sample/(Amount of IgG in first sub-sample+Amount of IgG in second sub-sample)

The samples in the above methods are contacted with EndoS polypeptide or alternative IgG-binding reagent under conditions suitable for interaction between the polypeptide or reagent and the sample to take place and IgG binding activity to occur. Suitable conditions are, for example, equivalent to those set out in the preceding section.

Method for Isolating IgG Fab or Fc Fragments from an IgG-Containing Sample

The methods of the present invention can be used for isolating Fab fragments from IgG-containing samples. In one embodiment, the present invention provides a method for isolating Fab fragments of IgG from an IgG-containing sample, which method comprises:
(a) contacting said IgG-containing sample with IdeS, and an Fc binding protein;
(b) separating said IdeS and said Fc binding protein from the contacted sample; and
thereby isolating Fab fragments.

Preferred methods for separating IdeS and Fc binding protein from a sample comprises using an IdeS and/or Fc binding protein which is derivatised or modified as described above. The same or a different modification may be used on each of IdeS and the Fc binding protein.

A preferred modification comprises the addition of a histidine tag. The presence of a histidine tag means that the polypeptide binds with a high affinity to a reagent or separating means containing chelating groups on its surface which carry a nickel, copper or zinc ion. The histidine tag binds strongly to these metal ions. Such a reagent can therefore be used to separate IdeS and/or Fc binding protein from a sample.

Another preferred modification comprises the addition of a biotin tag. The presence of a biotin tag means that the polypeptide binds with a high affinity to a reagent or separating means comprising streptavidin. The biotin tag binds strongly to streptavidin. Such a reagent can therefore be used to separate IdeS and/or Fc binding protein from a sample.

Preferred reagents or separating means are populations of magnetic particles capable of binding to the EndoS polypeptide. For example, where the IdeS and/or Fc binding protein polypeptide is derivatised with a histidine tag, the magnetic particles contain on their surface chelating groups which carry a nickel, copper or zinc ion. Alternatively, where the IdeS and/or Fc binding protein polypeptide is derivatised with a biotin tag, the magnetic particles contain on their surface streptavidin.

Accordingly, a preferred method of removing EndoS from a sample comprises using a population of magnetic particles as described above and carrying out magnetic field separation on the sample. The magnetic particles are preferably magnetic nanoparticles, and the magnetic field separation is preferably high-gradient magnetic field separation.

Thus, step (a) of the above method preferably additionally comprises contacting the sample with a population of magnetic nanoparticles capable of binding to IdeS and the Fc binding protein, and wherein step (b) comprises carrying out magnetic field separation on the sample.

It will be understood that any suitable separation means may be used. For example, the alternative means described in the section relating to methods for isolating a population of cells which are substantially free of IgG molecules bound to FcγRs could be adapted for separation of IdeS and/or Fc-binding protein.

The Fc binding protein is preferably Protein H or a modified EndoS polypeptide lacking endoglycosidase activity.

In the above embodiment of the invention, the IgG-containing sample typically comprises purified or isolated IgG. By "purified or isolated IgG" is meant an IgG fraction with a purity of normal commercial grade. IgG is typically isolated from a sample such as serum or, in the case of recombinant IgG, from cell lysate. Isolation may be carried out according to any suitable method, preferably according to the method described above for the isolation of IgG using a modified EndoS polypeptide lacking endoglycosidase activity. Thus, one embodiment of the invention encompasses the method set out above comprising, prior to step (a):
(i) contacting said IgG-containing sample with an EndoS polypeptide which lacks IgG endoglycosidase activity, to thereby allow formation of a IgG-EndoS polypeptide complex;
(ii) separating said IgG-EndoS polypeptide complex from the contacted sample;
(iii) eluting IgG from the IgG-EndoS polypeptide complex thereby obtaining an IgG-containing sample;
and wherein steps (a) and (b) are carried out the IgG-containing sample obtained in step (iii). Separation of the IgG-EndoS polypeptide complex from a sample is preferably carried out according to the methods set out in the section above relating to methods for determining the presence or absence of IgG in a sample, or for isolating IgG from an IgG-containing sample.

In an alternative embodiment of the invention, the methods are adapted to isolate Fab fragments from IgG-contained samples without the need to purify the IgG before carrying out the method. These methods can be carried out on a sample containing unpurified IgG, for example, whole serum, cell lysate or cell culture medium. In this embodiment of the invention, the method comprises:
(a) contacting said IgG-containing sample with an Fc binding protein to thereby allow formation of a IgG-Fc binding protein complex;
(b) separating said IgG-Fc binding protein complex from the contacted sample;
(c) adding to IgG-Fc binding protein complexes obtained in step (b) IdeS; and
(d) separating said IdeS and said Fc binding protein from the mixture obtained in (c);
and thereby isolating Fab fragments.

The methods for separating IdeS and/or Fc binding protein from the samples/mixtures above preferably comprise using an IdeS and/or Fc binding protein which is derivatised or modified as described above. The same or a different modification may be used on each of IdeS and the Fc binding protein. Preferred reagents or separating means are populations of magnetic particles capable of binding to the IdeS and/or Fc binding protein. For example, where the IdeS and/or Fc binding protein polypeptide is derivatised with a histidine tag, the magnetic particles contain on their surface chelating groups which carry a nickel, copper or zinc ion. Alternatively, where the IdeS and/or Fc binding protein polypeptide is derivatised with a biotin tag, the magnetic particles contain on their surface streptavidin.

Thus, step (a) of the above method preferably additionally comprises contacting the sample with a population of magnetic nanoparticles capable of binding to the Fc binding protein, step (c) additionally comprises contacting the IgG-Fc binding protein complexes obtained in step (b) with a population of magnetic nanoparticles capable of binding to IdeS and the Fc binding protein, and wherein steps (b) and (d) comprise carrying out magnetic field separation on the sample of (a) and mixture obtained in (c), respectively.

It will be understood that any suitable separation means may be used. For example, the alternative means described in the section relating to methods for isolating a population of cells which are substantially free of IgG molecules bound to FcγRs could be adapted for separation of IdeS and/or Fc-binding protein.

The Fc binding protein in the above embodiment is preferably Protein H or a modified EndoS polypeptide lacking endoglycosidase activity.

The above methods of the invention can also be used for isolating Fc fragments from IgG-containing samples. In one such embodiment of the invention, the method comprises:
(a) contacting said IgG-containing sample with IdeS;
(b) separating IdeS from the mixture obtained in step (a), thereby isolating Fab and Fc fragments;
(c) contacting said Fab and Fc fragments with an Fc binding protein to thereby allow formation of a Fc fragment-Fc binding protein complex;
(d) separating the Fc fragment-Fc binding protein complexes from the mixture obtained in step (c); and
(e) isolating Fc fragments from the Fc fragment-Fc binding protein complexes obtained in step (d).

It will be understood that any suitable separation means may be used as described above, however, the methods for separating IdeS and/or Fc binding protein from the samples/mixtures above preferably comprise using an IdeS and/or Fc binding protein which is derivatised or modified as described above.

Preferably, step (a) of the above method additionally comprises contacting the sample with a population of magnetic nanoparticles capable of binding to IdeS, step (c) additionally comprises contacting the Fab and Fc fragments obtained in step (b) with a population of magnetic nanoparticles capable of binding to the Fc binding protein, and wherein steps (b) and (d) comprise carrying out magnetic field separation on the sample of (a) and mixture obtained in (c), respectively. The Fc binding protein is preferably Protein H or a modified EndoS polypeptide lacking endoglycosidase activity.

In an alternative embodiment, Fc fragments may be isolated from an IgG-containing sample by a method comprising:
(a) contacting said IgG-containing sample with IdeS and an Fc-binding protein
(b) separating the Fc-binding protein from the mixture obtained in (a); thereby isolating Fc fragments.

It will be understood that any suitable separation means may be used as described above. However, preferably step (a) of the above method additionally comprises contacting the sample with a population of magnetic nanoparticles capable of binding to the Fc-binding protein but not to IdeS, and wherein step (b) comprises carrying out magnetic field separation on the mixture obtained in (a). Preferably, the IdeS and/or the Fc-binding protein are derivatised or modified as described above, with the proviso that a different modification is applied to each. For example, where the IdeS is modified by addition of a histidine tag such that it binds to a population of magnetic particles containing on their surface chelating groups which carry a nickel, copper or zinc ion, the Fc-binding protein might be modified by addition of a biotin tag such that it binds to a population of magnetic particles containing on their surface streptavidin. The Fc binding protein is preferably Protein H or a modified EndoS polypeptide lacking endoglycosidase activity.

Similar to the methods for isolating Fab fragments, it will be appreciated that in the methods for separating Fc fragments the IgG-containing sample typically comprises purified or isolated IgG. A preferred method of isolating IgG is described in steps (i) to (iii) as set out above.

Kits

The present invention provides:
a kit for isolating a population of cells substantially free of Fcγ-receptor-bound IgG molecules, comprising:
(a) an EndoS polypeptide according to the invention with endoglycosidase activity; and optionally
(b) means and/or instructions for separating cells from a sample.

a kit for isolating IgG from an IgG-containing sample, comprising:
(a) an EndoS polypeptide according to the invention which lacks endoglycosidase activity; and optionally
(b) means for separating said EndoS polypeptide from a sample.

a kit for determining the presence or absence of IgG in a sample, comprising:
(a) an EndoS polypeptide according to the invention which lacks endoglycosidase activity; and optionally
(b) means for separating said EndoS polypeptide from a sample.

a kit for assessing the glycosylation state and/or functional quality of an IgG containing sample, comprising:
(a) an EndoS polypeptide according to the invention which lacks endoglycosidase activity; and optionally;
(b) an alternative IgG-binding reagent which is capable of binding denatured and/or deglycosylated IgG;
(c) means for separating said EndoS polypeptide from a sample; and
(d) means for separating said alternative IgG-binding reagent from a sample.

The alternative IgG-binding reagent comprises Protein G and/or Protein A and/or Protein A/G.

The present invention also provides:
a kit for isolating Fab or Fc fragments of IgG comprising:
(a) IdeS;
(b) an Fc binding protein; and
(c) means for separating said IdeS and said Fc binding protein from a sample.

In a preferred embodiment, the kit additionally comprises an EndoS polypeptide according to the invention which lacks endoglycosidase activity and a means for separating said EndoS polypeptide from a sample. The Fc binding protein is preferably Protein H or an EndoS polypeptide according to the invention which lacks endoglycosidase activity.

Preferred embodiments of the above kits further comprise instructions for using the kit in a method of the invention. Further preferred embodiments include those wherein the means for separating an EndoS polypeptide, an alternative IgG-binding reagent, an IdeS polypeptide, or an Fc binding protein from a sample are populations of magnetic nanoparticles, wherein each population is capable of binding to at least one of the indicated polypeptides/reagents/proteins. In this embodiment the kit typically additionally comprises instructions to perform magnetic field separation on the sample.

In preferred embodiments of the above methods and kits, the polypeptides/proteins/reagents used are derivatised with an affinity tag, preferably a histidine tag, to assist with separation of said polypeptides.

The following Examples illustrate the invention:

Example 1

In the present study we elucidate the effect(s) of EndoS on IgG subclasses and IgG-FcgR interactions. The results revealed that EndoS hydrolyses the heavy chain of all four human IgG subclasses ($IgG_{1-4}$), both soluble and in a plasma environment. Additionally, we found that EndoS hydrolysis of the IgG glycan dramatically influences the binding of IgG to soluble, immobilized FcγRIIa and FcγRIIb as well as to FcγR-expressing cells. Moreover, IgG bound to these cells dissociates due to treatment of cells with EndoS. Furthermore, an intact form of EndoS generated by site-directed mutagenesis binds with high affinity to $IgG_{1-4}$, while the active form only transiently interacts with its substrates. These results provide novel information about the mechanisms behind enzymatic modulation of the host immune defense by bacteria, provide novel information about the molecular interactions between an IgG glycan-hydrolyzing enzyme and IgG, and emphasize the importance of IgG glycosylation for correct antibody effector functions.

Materials and Methods
Proteins and Reagents

Blood was drawn from healthy individuals and collected in heparin containing tubes. Full-length EndoS with (GST-EndoS) or without glutathione-S-transferase (GST) as a fusion was recombinantly expressed and purified from *Escherichia coli* harboring the plasmid pGEXndoS. The mutation of glutamic acid 235 of EndoS into glutamine was performed as follows:

Mutation of glutamic acid 235 (Glu-235) into glutamine (E235Q) was performed using QuickChange II Site-Directed Mutagenesis Kit (Stratagene, La Jolla, Calif.). The mutagenic oligonucleotide primers (mutation underlined) 5'-CCT TGA TGG CTT AGA TGT GGA TGT TCA ACA TGA TAG TAT TCC-3' (SEQ ID NO: 7) and the anti-sense of the above sequence were allowed to anneal to denatured plasmid pGEXndoS. Mutated strands were amplified using high fidelity DNA and parental methylated strands were digested with DpnI. This was followed by transformation into supercompetent *E. coli* XL-1 Blue for nick repair and replication, generating mutated plasmid pGEXndoS(E235Q). Recombinant EndoS(E235Q) was then expressed and purified as described above for EndoS.

Soluble purified Fc-receptors were generated by co-transfection of CHO-K1(CHO) cells with pNT-neo-FcγRII or pNT-neo-FcγRIII plasmids with subsequent selection in 1 mg/ml genetecin. IgG-subclasses were purified from human plasma as described (Ref). RPMI 1640 medium and Hank's balanced salt solution (HBSS) were from GIBCO, Paisley, U.K. All other reagents were purchased from Sigma-Aldrich unless indicated otherwise.

Treatment of Human Plasma with EndoS and Purification of IgG

A volume of 2 ml human plasma was incubated with 20 μg EndoS or PBS for 1.5 hours at 37° C. The IgG fraction was purified using Protein G Sepharose (GE Healthcare Bio-sciences AB, Uppsala, Sweden). Briefly, 200 μl Protein G Sepharose suspended 1:1 in PBS (phosphate-buffered saline; 10 mM phosphate buffer, pH 7.4, 120 mM NaCl, 3 mM KCl) was added to plasma samples and incubated at 4° C. for 2 hours or over night. After centrifugation for five minutes at 8000×g, the supernatant was discarded and the pellet washed three times with PBS. IgG was eluated with 0.1 M glycine pH 2.0 and neutralized with 1 M Tris-HCl pH 8.0. The IgG concentration was determined to 8 mg/ml using the Advanced Protein Assay (Cytoskeleton, Denver, Colo., USA).

Cell Preparations

The K562 cell line was cultured in RPMI 1640 medium supplemented with Glutamax-I, 100 μg/ml antibiotics (penicillin and streptomycin) and 10% fetal calf serum at 37° C. in an atmosphere containing 5% $CO_2$ and 95% humidity. Nunclon flasks for cell culture were used (Nunc A/S, Roskilde, Denmark). Cells were cultured in a serum free medium for 20 hours before being used in experiments. Monocytes were isolated from human whole blood using the Polymorphprep preparation kit (AXIS-SHIELD, Oslo, Norway) or Ficoll-Paque Plus (Amersham Bioscience, Uppsala, Sweden) according to instructions provided by the manufacturers. After isolation, cells were counted and resuspended in PBS or RPMI-medium.

Enzyme Linked Immunosorbent Assay (ELISA)

For glycan detection, microtiter plates (NUNC, Roskilde, Denmark) were coated with 100 µL monoclonal mouse anti-human IgG1, IgG2, IgG3 or IgG4 (SIGMA®, Saint Louis, Mo., USA) diluted to final concentrations of 1.5-0.5 µg/ml in coating buffer containing 16 mM $Na_2CO_3$ and 35 mM $NaHCO_3$, pH 9.6 and kept at 4° C. overnight. Then, the plate was washed three times with lectin buffer containing 10 mM HEPES, pH 7.5, 0.15 M NaCl, 0.01 mM $MnCl_2$, 0.1 mM $CaCl_2$ and 0.1% v/v Tween 20 and blocked in the same buffer for one hour at room temperature. In the next step purified IgG fraction (dilution 1:100) was added and the incubation proceeded for another 2 hours at 37° C. After three washes with lectin buffer, 1 µg/ml biotinylated *Lens Culinaris* agglutinin (LCA)-lectin (Vector Laboratories, Burlingame, Calif., USA) was added and incubation continued for 1 hour at 37° C. Following three more washes, 0.1 µg/ml peroxidase-labeled streptavidin (Vector Laboratories) was added and the plate was incubated for 1 hour at 37° C. The color reaction was developed with 0.1 M citric acid monohydrate, 0.1 M $Na_2HPO_4 \times 2H_2O$ buffer pH 4.5 containing 0.012% v/v $H_2O_2$ and 1.7 mM 2,2'-azino-bis(3-ethylbenzthiazoline-6-sulphonic acid) (ABTS). The absorbance was read on a model 550 micro plate reader (BIO-RAD, Hercules, Calif., USA) at 415 nm. For detection of binding of human IgG subclasses to FcγRs, the plate was coated with soluble FcγRIIa or FcγRIIb or FcγRIIIa at a concentration 5 µg/ml for 20 hours at 4° C. Next day, the plate was blocked with PBS supplemented with 0.05% v/v Tween 20 (PBST) and 2% w/v bovine serum albumin for 2 hours at room temperature. After this step, the purified IgG subclasses, 0.1 µg of each were added. The plate was washed three times with PBST after the coating step and between each of the following incubation step. A peroxidase-conjugated protein G (dilution 1:5000) (BIO-RAD, Hercules, Calif., USA) was used for detection. The color reaction was performed as above. All experiments were made in triplicates.

Radioactive Labeling

Proteins were labelled with 0.2 mCi Na $^{125}$I (PerkinElmer, Upplands-Väsby, Sweden) using the IODE-BEADS Iodination reagent kit (PIERCE, Rockford, Ill., USA) according to manufacturer's instructions. The unbound radioactivity was removed by desalting the proteins on PD-10 Sepharose (Pharmacia, Sweden). The activity of the labeled proteins was estimated to 4 µCi/µg protein.

Detection of IgG Binding to Cells

IgG was purified from human plasma treated with EndoS or PBS as described above and thereafter labeled with $^{125}$iodine ($^{125}$I) For detection of $^{125}$I-IgG binding to K562 cells, $2 \times 10^6$ cells were incubated with $0.5 \times 10^6$ cpm of $^{125}$I-IgG or $^{125}$I-deglycosylated IgG for 30 minutes at room temperature. After five washes with PBS and centrifugations at 1000×g for three minutes, the radioactivity of the cell pellets was detected using Wallac Wizard™ 1470 Automatic Gamma Counter (PerkinElmer, Waltham, Mass., USA). In another experiment, $1 \times 10^6$ monocytes were incubated with $0.5 \times 10^6$ cpm of $^{125}$I-IgG or $^{125}$I-EndoS treated IgG for 30 minutes at room temperature. After five repeated washes of cells with PBS and final pelleting of cells by centrifugation at 1000×g for five minutes, the cells were resuspended in lysis buffer containing 20 mM Tris-HCl pH 7.4, 0.150 M NaCl, 1% v/v Triton-100 and 0.25% v/v NP40 for ten minutes at 4° C. Next, the samples were centrifuged for ten minutes at 14000×g and supernatants applied on a polyacrylamide gel. After separation, the gel was dried and samples analyzed by phosphoimaging in a Fujix BAS 2000 Bioimaging analyzer (Fujifilm Sverige AB, Stockholm, Sweden). In experiment when the binding of IgG to cells was analyzed by Western blot, $0.5-1 \times 10^6$ cells were incubated with plasma treated with EndoS or buffer (as described above), at 37° C. for 1 hour. Afterwards, the cells were washed three times with PBS or RPMI medium, resuspended in 100 µL lysis buffer and the bound IgG in cell lysates analyzed by Western blot.

Incubation of Cells with EndoS

K562 cells or monocytes, $2 \times 10^6$ and $8 \times 10^6$ respectively, were incubated with two ml of human plasma for 30 minutes at 37° C. The cells were washed five times with PBS and centrifuged at 1000 g for ten minutes after every wash. EndoS, 40 µg in PBS or PBS alone was added to cells and incubation followed for one hour at 37° C. Cells were washed three times with PBS and resuspended in 100 µL lysis buffer. Samples were centrifuged for five minutes at 14000×g, and pellets discarded and supernatants saved for analysis. The supernatants were analyzed for IgG and glycan contents using SDS-PAGE and Western blot.

Slot-Blotting Analysis

IgG1-4, 0.3, 015, 0.075 µg of each in PBS were applied to PVDF membranes using a slot-blot apparatus from Schleicher and Schuell, Inc., Kene, N.H. 03431, USA. The membranes were incubated with PBST, 5% skim milk, for 1 hour, washed with PBST and incubated with EndoS or EndoS (E235Q), 0.05 mg/ml in PBST and 5% skim milk for 1 hour. After washing, the membranes were incubated with rabbit EndoS-antiserum and subsequently with peroxidase conjugated goat anti-rabbit antibodies. The color development was made using ABTS as peroxidase substrate. All incubation steps were performed at room temperature.

BIAcore Surface Plasmon Resonance Interaction Analysis

Receptors, IgGs and deglycosylated IgGs were diluted with 10 mM sodium acetate pH 4 and immobilized via amine coupling to different flow cells of CM5 sensorchips (BIAcore, Uppsala, Sweden). Immobilization levels were optimized to around 8000-10000 response units. After determining EndoS(E235Q) as a non-binder to all deglycosylated IgG variants, these flow cells were considered as controls for bulk refraction index changes for EndoS(E235Q) binding to IgG1 throughout IgG4, respectively. In experiments determining IgG1-IgG4 affinity for the receptors FcγRIIa, FcγRIIb and FcγRIIIa, a flow cell subjected to the immobilization protocol but without addition of protein was used as control. For affinity measurements, the binding and dissociation phases were monitored in a BIAcore 2000 instrument. In control experiments for possible mass transfer limitations, the IgGs were injected over the receptors and the EndoS variants over the IgG sub-classes at different flow rates. No differences in initial binding were observed at 5 µl/min or above indicating no limitations to any combinations. Interactants were injected in different concentrations (typically 10-1.25 µg/ml) at 35 µl/min and 25° C. over the different coated surfaces (flow cells) (in running buffer: 10 mM Hepes, pH 7.5, 150 mM NaCl, 0.005% surfactant P20, and 3.4 mM EDTA). Between experiments, the surfaces were strictly regenerated with pulses of running buffer containing 2 M NaCl followed by an extensive wash procedure after reaching baseline. For EndoS digestion of IgG bound to pre-immobilized FcγRIIa, an IgG1 concentration (10 µg/ml) was chosen to give a suitable steady-state dissociation phase at a time point were the IgG1 injection was aborted and replaced by running buffer. This experiment was considered as a control and as such compared to an EndoS injection at the same time point after IgG1 binding to FcγRIIa. After X and Y normalization of data, the blank curves from control flow cells of each injected concentration were subtracted. Where applicable, the association ($k_a$) and dissociation ($k_d$) rate constants were determined simultaneously using the equation for 1:1 Langmuir binding in the BIA Evaluation 4.1 software (BIAcore). The binding curves were fitted locally and the equilibrium dissociation constants ($K_D$) were calculated from mean values of the obtained rate constants.

Flow Cytometry Analysis of Whole Blood

A volume of 15 ml blood was incubated with 0.4 mg EndoS or PBS for 35 minutes at 37° C. An activator of leukocytes, Formyl-Methionine-Leucine-Phenylalanine (fMLP), (dilution 1:10000) (SIGMA, Saint Louise, Mo., USA) was then added and the incubation continued for 10 minutes at 37° C. Next, blood samples were centrifuged 1000 g, five minutes. Plasma and buffy coat was transferred to another tube and centrifuged for five minutes at 1000 g. The cells were then washed three times with HBSS containing 30% v/v RPMI and finally resuspended in 100 µl of the same medium. Monoclonal mouse anti-human IgG was prepared by mixing equal amounts of mouse anti-human IgG1 (51 mg/ml), IgG2 (22 mg/ml), IgG3 (16 mg/ml) and IgG4 (24 mg/ml) and 5 µl of this mixture was added and samples incubated for ten minutes at room temperature. In the next step 5 µl of FITC-conjugated goat anti-mouse IgG (DakoCytomation, Glostrup, Denmark) was added before erythrocytes were lysed using the DakoCytomation Uti-Lyse erythrocyte kit (Carpinteria, Calif.). Signals were analyzed on a FACSCalibur flow cytometer (Becton Dickinson, Franklin Lakes, N.J., USA). Monocytes were identified by forward scatter and side scatter characteristics (FSC/SSC).

SDS-PAGE and Western Blot Analysis

Sodium dodecyl sulfate-polyacrylamide gel electrophoresis (SDS-PAGE) was performed using Mini Protean II cell equipment from BIO-RAD (Hercules, Calif., USA) or equipment from LKB produkter (Bromma, Sweden) using the buffer system described by Laemmli (17). Samples were mixed 1:1 (v/v) with sample buffer supplemented with 5% mercaptoethanol, and boiled for five minutes before loading onto the 10% polyacrylamide gel. PageRuler™ Protein Ladder Plus (Fermentas, Burlington, Canada) was used as high-molecular-mass standards. The polyacrylamide gels were stained with Coomassie Brilliant Blue R-250 and in some cases dried. For immunoblotting, the gels were transferred to polyvinylidenefluoride (PVDF) membranes (Immobilon P, Millipore, Bedford, Mass.) as described by Matsudaira (18). After blotting, membranes were blocked in PBS supplemented with 0.05% v/v Tween 20 (PBST) and 5% w/v skim milk (DIFCO, Detroit, Mich.) for 20 minutes at room temperature. For detection of IgG, the blots were subsequently washed in PBST and then incubated with rabbit anti-human IgG (diluted 1:3000) (BIO-RAD, Hercules, Calif.) for one hour at 37° C. After a washing step, membranes were incubated with horseradish peroxidase-conjugated goat anti-rabbit IgG (BIO-RAD) (dilution 1:1000). For lectin blot analysis, membranes were blocked for 20 minutes in lectin buffer, 10 mM HEPES, pH 7.5, 0.15 M NaCl, 0.01 mM $MnCl_2$, 0.1 mM $CaCl_2$ and 0.1% v/v Tween 20 at room temperature and incubated with biotinylated LCA lectin (Vector Laboratories) (diluted 1:5000). After repeated washes in lectin buffer the membranes were incubated with peroxidase-labeled streptavidin (Vector Laboratories) (diluted 1:10000). All membranes were developed using SuperSignal West Pico (PIERCE, Rockford, Ill.) according to the manufacturer's instructions before analyzing by the Chemidoc XRS imaging system and Quantity One image analysis software (BIO-RAD).

Results

EndoS has Glycosidase Activity on all Four IgG Subclasses

Figure 2:
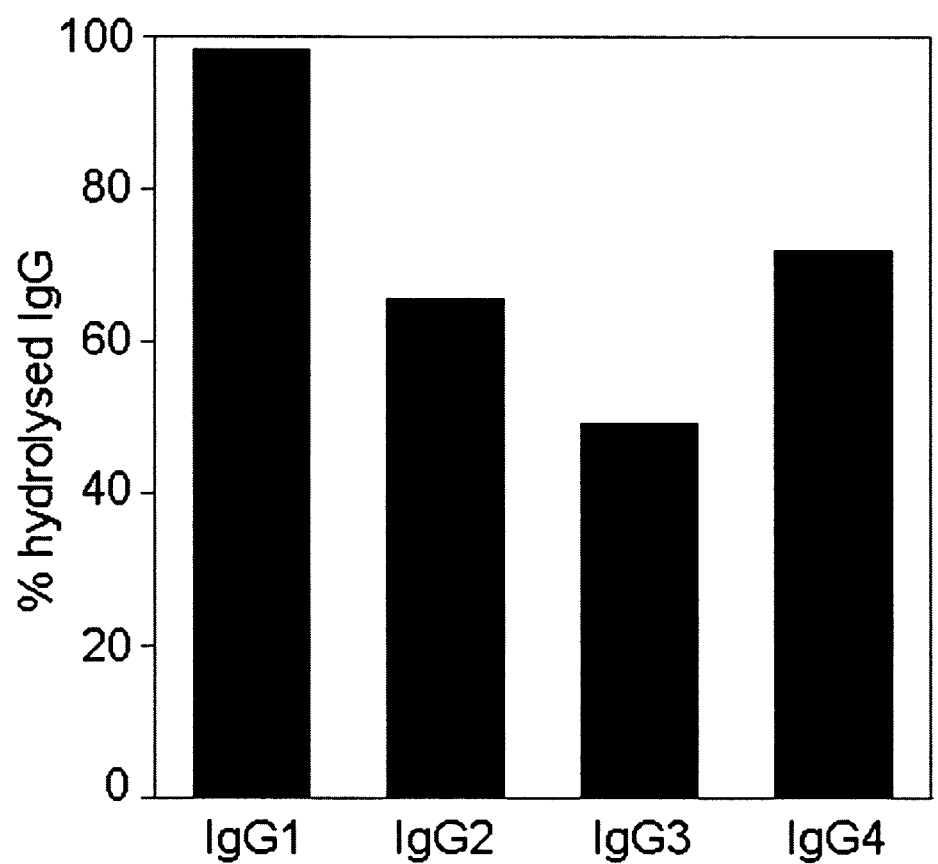
FIG. 2 shows the hydrolysis of human IgG-subclasses by EndoS in a plasma environment. Human plasma treated with EndoS or PBS and followed by LCA lectin ELISA of the purified IgG fraction. IgG glycan hydrolysis was detected using LCA lectin ELISA. The results are presented as percent hydrolysis of each subclass compared to signals from untreated plasma.

It has previously been shown that EndoS hydrolyzes the chitobiose core of the conserved N-linked glycan on the γ-chain of human polyclonal IgG (FIG. 1A). It was therefore of interest to elucidate whether EndoS has activity on all four subclasses of human IgG ($IgG_{1-4}$). Purified recombinant EndoS was incubated with purified human $IgG_{1-4}$. SDS-PAGE analysis revealed that EndoS-treated IgG of all subclasses migrated at an apparent molecular weight of approximately 3 kDa lower than untreated IgG (FIG. 1B), which is consistent with hydrolysis of the chitobiose core of the IgG glycan. To confirm glycan hydrolysis, samples were also analyzed by lectin blot using a Lens culinaris agglutinin (LCA) lectin recognizing α-linked mannose residues (FIG. 1A). Lectin blot analysis of the samples revealed that all IgG subclasses lose the reactivity with LCA after incubation with EndoS consistent with complete or nearly complete hydrolysis of the glycan (FIG. 1C). Additionally, the glycosidase activity of EndoS on $IgG_{1-4}$ in a plasma environment was investigated. In this experiment human plasma was incubated with purified EndoS or buffer, followed by affinity purification of the IgG fraction. These fractions were subsequently subjected to a LCA ELISA using immobilized monoclonal antibodies against $IgG_{1-4}$ to capture IgG. This revealed that all four IgG subclasses reacted with lectin when plasma was incubated with buffer (control), indicating presence of the glycan. In contrast, when plasma was treated with EndoS, a significantly reduced $IgG_{1-4}$ reactivity with LCA lectin was observed, indicating hydrolysis of the glycan on $IgG_{1-4}$ (FIG. 2). Taken together, these results clearly show that EndoS has the ability to hydrolyze human IgG of all subclasses, in purified form as well as in whole plasma.

Inactive Form of EndoS Binds IgG

Figure 3:
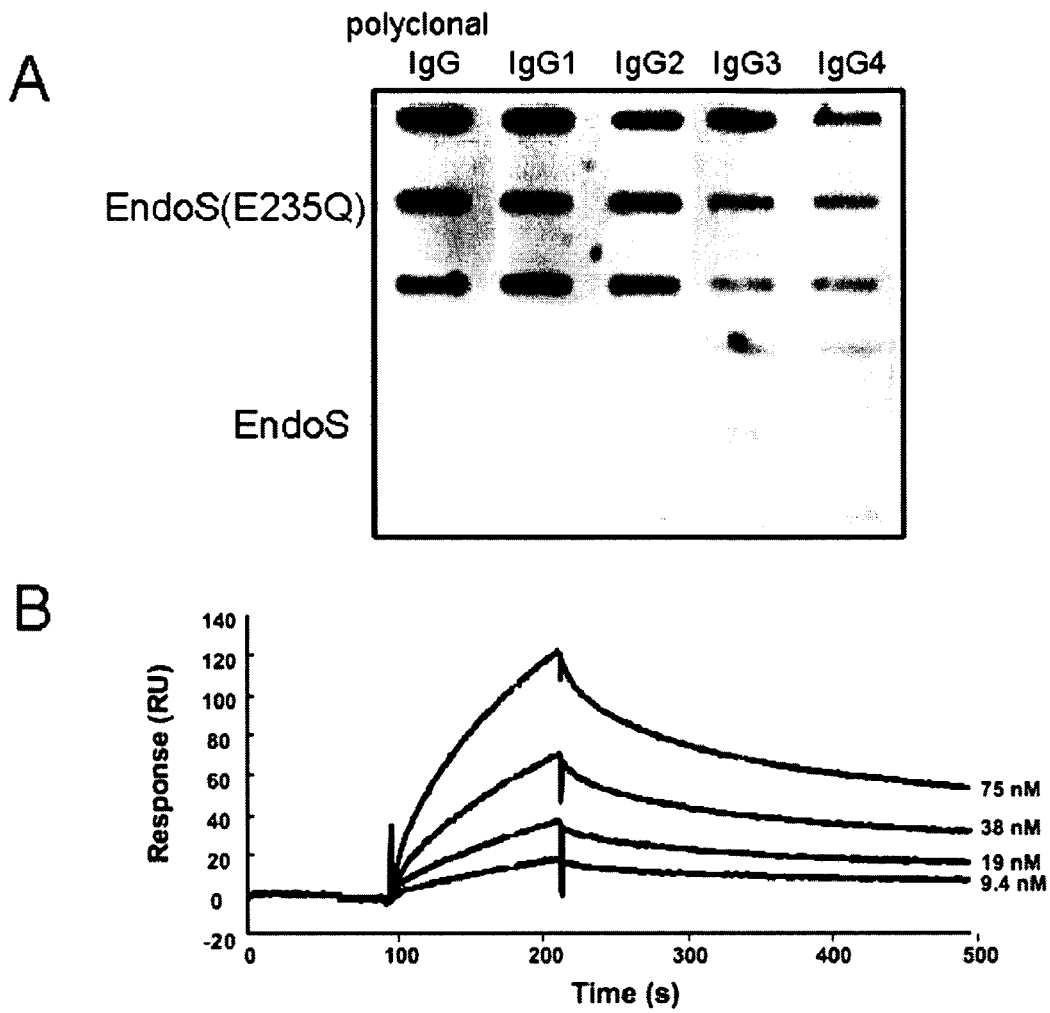
FIG. 3 shows that EndoS(E235Q) binds to all IgG-subclasses. Panel A: Slot-blot representing the binding of EndoS and EndoS (E235Q) to each IgG subclass immobilized onto a nitrocellulose membrane in amounts: 3, 1.5 and 0.75 µg. The binding was detected using antiserum against EndoS. Panel B: Binding of EndoS (E235Q) to immobilized IgG-classes using BIAcore technology. The selected plot shows EndoS (E235Q) binding to IgG1 using hydrolysed IgG1 as a reference (bulk changes subtracted). Binding kinetic constants are shown in the table where applicable. Nb indicates that the combination is investigated but shown not to bind using the BIAcore technology.

We have previously partly elucidated the molecular requirements for EndoS hydrolysis of IgG. Site directed mutagenesis of glutamic acid 199 of SEQ ID NO: 1 (position 235 of SE ID NO:3) (EndoS(E235Q)) to glutamine at the proposed orifice of the catalytic tunnel abolishes enzymatic activity. In addition, chemical blocking of tryptophanes revealed that these amino acid residues are important for activity. To further investigate the physical interaction between enzyme and substrate, the binding of EndoS and EndoS(E235Q) to immobilized polyclonal IgG and $IgG_{1-4}$ subclasses was studied using slot-binding experiments with immobilized IgG probed with EndoS and EndoS(E235Q). Purified, soluble IgG subclasses 1-4, each immobilized onto a nitrocellulose membrane, were probed with EndoS and EndoS (E235Q) followed by incubation with antibodies against EndoS. This experiment revealed a strong binding of EndoS (E235Q) to polyclonal IgG, IgG1 and IgG2, and a weaker association to IgG3 and IgG4, while only very weak interactions between active EndoS and all subclasses could be seen (FIG. 3A). To calculate the affinity constants between EndoS and immobilized $IgG_{1-4}$, surface plasmon resonance was used. Similarly to slot-binding results, this showed that EndoS (E235Q) binds all IgG subclasses with high affinity, while there is no detectable binding of EndoS to IgG. (FIG. 3B, Table 1). The kinetic parameters of EndoS (E235Q) binding to immobilized IgG subclasses were of similar character and the strongest interaction was demonstrated between IgG1 and EndoS(E235Q) with a binding affinity constant ($K_D$) of 0.42 µM. No binding of either EndoS or EndoS(E235Q) to $IgG_{1-4}$ subclasses, which were hydrolysed by EndoS before immobilization, was detected. These findings indicate that the intact IgG glycan is necessary for the interaction between EndoS and IgG. Furthermore, the experiments comparing the interactions between EndoS, EndoS(E235Q) and IgG indicates that EndoS binds IgG with a high affinity, but the active enzyme is instantly released after glycan hydrolysis in a "touch and go" manner.

EndoS Influences the Binding of IgG$_{1-4}$ to FcγRs

Figure 4:
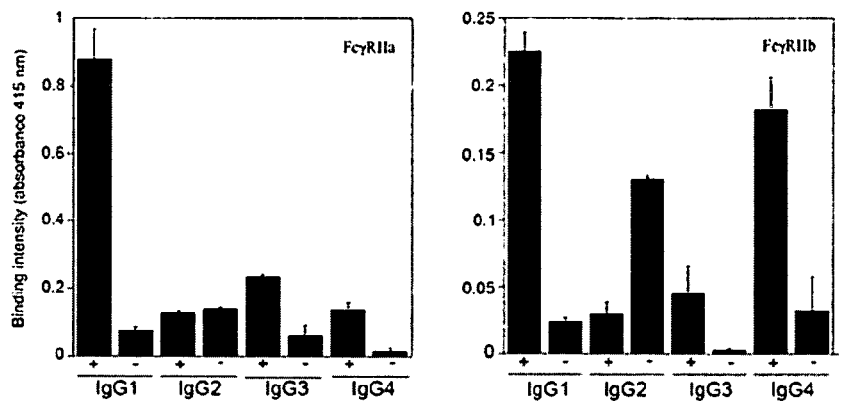
FIG. 4 shows that EndoS treatment of IgG subclasses inhibits binding of IgG to FcγRII. Panel A: Binding of purified IgG subclasses, EndoS treated or not, to FcγRIIa and FcγRIIb immobilized to a microtiter plate. HRP-labeled protein G was used for detection of bound IgG subclasses. (+) indicates intact IgG and (−) EndoS hydrolysed IgG. Panel B: Binding of IgG subclasses to immobilized receptors as visualized using BIAcore surface plasmon resonance. Plot shows a typical sensorgram, here the IgG1 binding to FcγRIIa. An empty flow cell is used as reference (subtracted). Data shown in Table 2 are kinetic constants of binding IgG-subclasses. Nb indicates that the IgG-receptor pair is investigated using the technology, but here shown not to interact.
Figure 4:
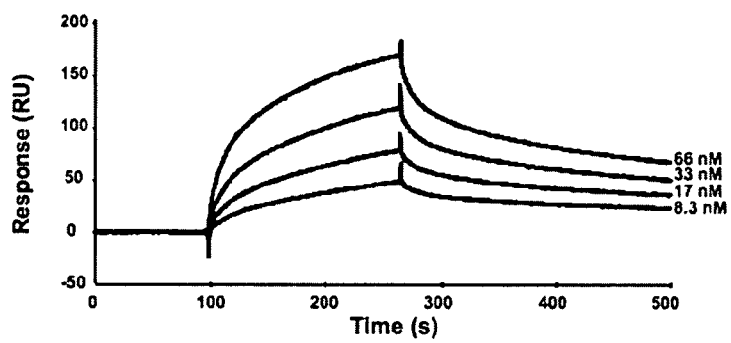

Since the nature of the interactions between FcγRs and the Fc domain of IgG is highly dependent on the IgG glycosylation state we explored the effects of EndoS activity on IgG interactions with FcγRs. Thus, in ELISA experiment the soluble FcγRIIa, FcγRIIb and FcγRIIIa were immobilized and probed with purified IgG$_{1-4}$ subclasses. In line with other observations it was here seen that FcγRIIa and FcγRIIb binds IgG1. This binding was nearly abolished after treatment of IgG1 with EndoS. The binding of the other IgG subclasses to these receptors was weak and was even more reduced after treatment with EndoS. In general, ELISA studies revealed the IgG subclass binding affinity pattern IgG1>IgG3>IgG4>IgG2 for FcγRIIa and IgG1>IgG4>IgG3>IgG2 for FcγRIIb (FIG. 4A). Furthermore, we observed that the EndoS hydrolysed IgG2 had a different outcome regarding the binding to FcγRIIa/FcγRIIb with more extensive binding ability, compared to the untreated IgG2. FcγRIIIa was negative in binding of all IgG subclasses (data not shown). The interaction between IgG$_{1-4}$, EndoS treated or not, with FcγRs was further analyzed by surface plasmon resonance. Each IgG subclass was captured on the surface with an immobilized FcγRIIa, FcγRIIb or FcγRIIIa. Consistent with the ELISA data, the results showed that IgG1 had the strongest affinity for both FcγRIIa and FcγRIIb with similar binding affinity constants, 97 nM and 17 nM respectively (FIG. 4B, Table 2). In agreement with our previous findings, no binding of IgG1 to these receptors was detectable when EndoS treated IgG1 was used. There was no detectable interaction between FcγRIIa/FcγRIIb and IgG2 or IgG3, or between IgG4 and FcγRIIa (Table 2). No binding of soluble IgG$_{1-4}$ subclasses to immobilized FcRIIIa could be detected. These results indicate that EndoS hydrolysis dramatically decreases IgG's affinity for FcγRs.

EndoS Decreases IgG Binding to Blood Cells

Figure 5:
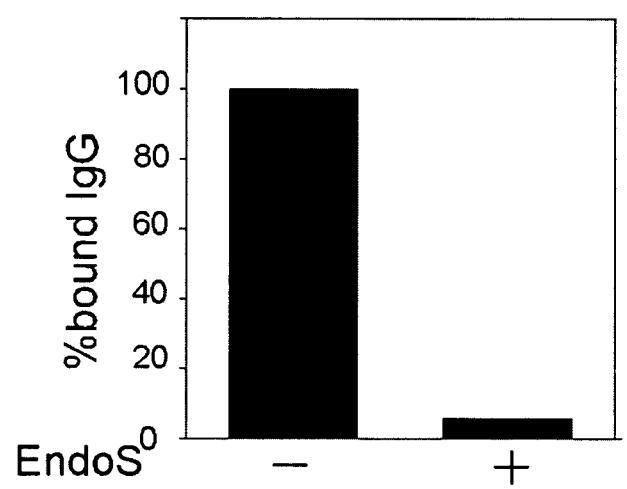
FIG. 5 shows that EndoS treated IgG does not bind to FcγRIIa on K562 cells. Panel A: The relative binding of radioactive IgG, treated with EndoS or not, to K562 cells. The cells were incubated with $^{125}$iodine-labelled IgG (intact or EndoS-treated). The radioactivity of the washed cell pellets was detected. The binding of $^{125}$I-IgG (intact) to K562 cells, presented here as 100%, represents a specific IgG binding to K562 cells that could be inhibited by addition of cold IgG. Panel B: K562 cells were incubated with human plasma treated with EndoS or PBS. The cells were resuspended in lysis buffer and analyzed by SDS-PAGE and Western blot using antiserum against human IgG.
Figure 5:
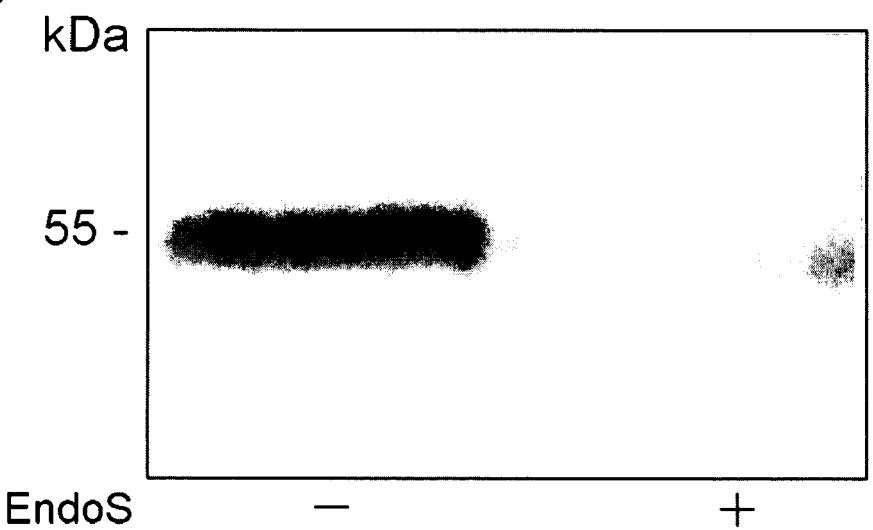
Figure 6:
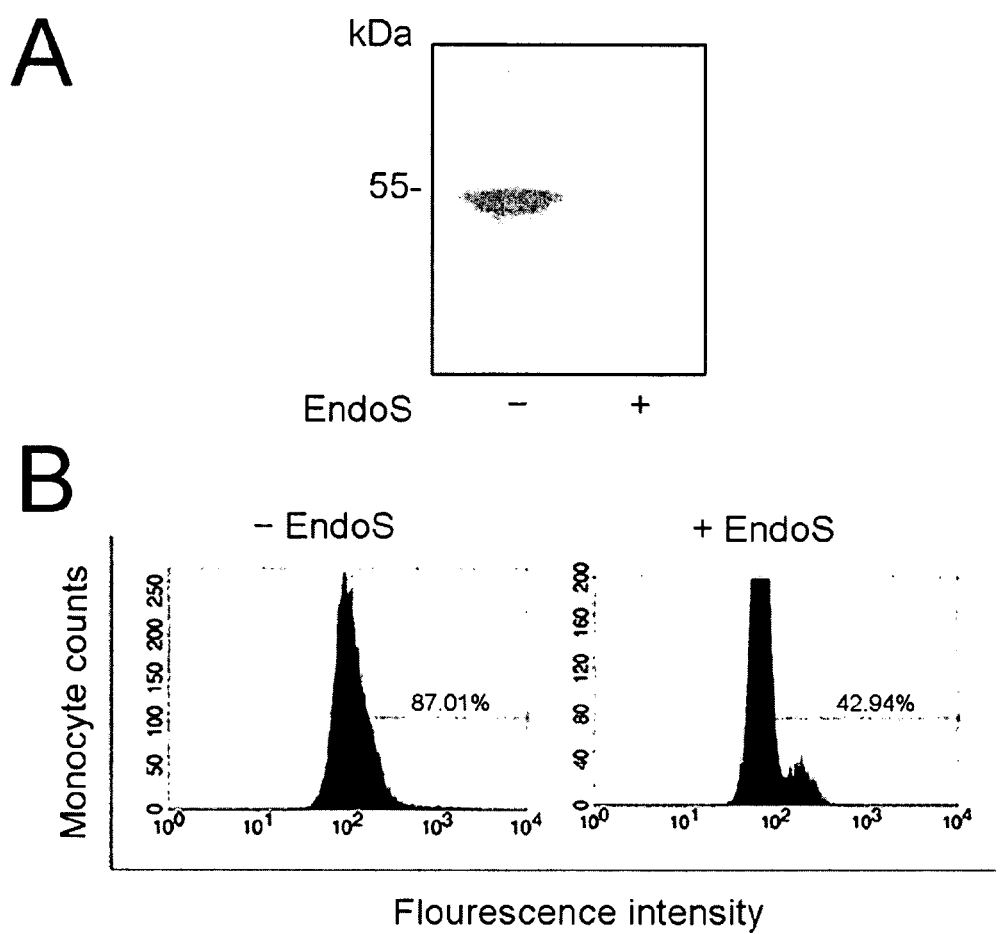
FIG. 6 shows that EndoS treated IgG does not bind to monocytes. Panel A: Monocytes were incubated with $^{125}$iodine-labelled IgG (intact or EndoS-treated). After incubation for 30 minutes at room temperature, the proteins from cell lysates, 10 µg total protein, were separated by 10% SDS-PAGE. The gel was dried and analyzed by phosphorimaging. Panel B: Flow cytometry analysis showing the decreased binding of IgG to activated monocytes in blood treated with EndoS. Human blood was treated with EndoS before addition of leukocyte activator fMLP. The IgG binding to monocytes was detected using mouse anti-human IgG and FITC-labelled goat anti-mouse IgG as a secondary antibody.

Based on results from ELISA and surface plasmon resonance, we continued to analyze the effect(s) of EndoS glycosidase activity on the interaction between FcγRs and IgG. For this purpose we used an erythroleukemic cell line (K562) exclusively expressing FcγRIIa. Since soluble FcγRI was not available to us, we also investigated human monocytes that predominantly bind IgG through FcγRI. Thus, IgG was purified from plasma treated with EndoS or PBS, labeled with $^{125}$I and incubated with the K562 cells. The radioactivity of the cell pellets was measured. The specific IgG binding to these cells was calculated by addition of cold human IgG which inhibited the binding of radioactive IgG. This showed that the binding of radioactive IgG, originally purified from plasma treated with EndoS, was totally abolished (FIG. 5A). A strong binding of IgG to K562 cells after incubation of cells with human plasma was confirmed by Western blot and the reactivity of cell lysates with antibodies against human IgG. In contrast, there was a clear decrease in binding of IgG to K562 cells incubated with plasma pre-treated with EndoS (FIG. 5B). Likewise, the binding of $^{125}$I-IgG to monocytes as analyzed by SDS-PAGE was totally inhibited when IgG was treated with EndoS (FIG. 6A). To further analyze EndoS' influence on the interaction between FcγRs on monocytes and IgG, flow cytometry analysis of whole blood was performed. Human blood was incubated with EndoS after pre-incubation of blood with the leukocyte activator fMLP. Monocytes were gated based on forward and side scatter and the reactivity of monocytes with monoclonal anti-human IgG was evaluated. The result revealed that 87% of monocytes were positive for IgG binding, while only 43% of monocytes in blood incubated with EndoS were positive (FIG. 6B). These results indicate that EndoS hydrolyzed IgG is significantly reduced in its binding capacity to human cells expressing different sets of FcγRs.

IgG Dissociates from FcγRIIa upon Treatment with EndoS

Figure 7:
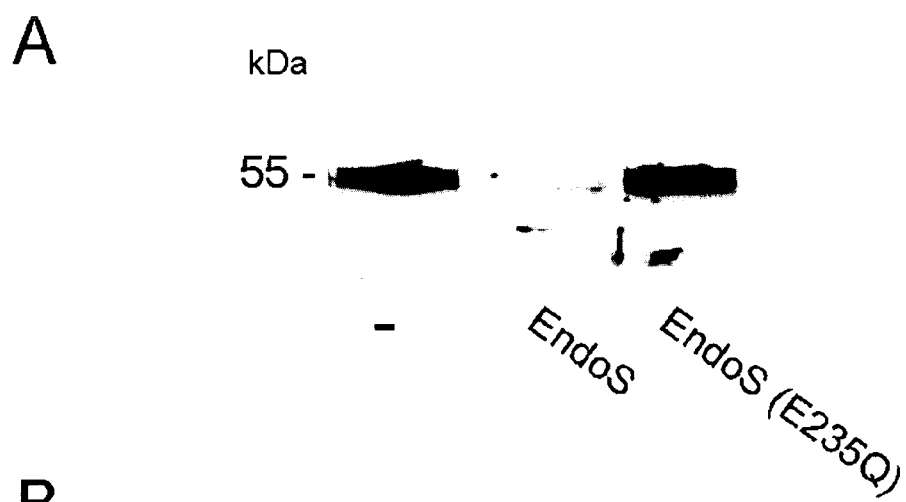
FIG. 7 shows the dissociation of IgG from FcγRII upon treatment with EndoS. Panel A: IgG bound to K562 cells dissociates from FcγRIIa upon incubation with EndoS but not with EndoS(E235Q). K562 cells were incubated with plasma and subsequently with EndoS, EndoS(E235Q) or PBS. Cell lysates, 10 µg total protein, were analysed for IgG by SDS-PAGE and blot using antiserum against human IgG. Panel B: IgG bound to monocytes dissociates from FcγRs after treatment with EndoS. Monocytes were incubated with plasma and later with EndoS or PBS. Resuspended cell pellets were analyzed for IgG by blot using antiserum against human IgG. The glycan of IgG was detected by blot and reactivity with LCA lectin. Panel C: A BIAcore setup showing EndoS affecting the IgG1 dissociation from an immobilized receptor FcγRIIa. In two parallel experiments, the injection of EndoS (black curve) is compared to the injection of buffer (broken line) at the same time-point during the dissociation phase of the IgG1-FcγRIIa interaction.
Figure 7:
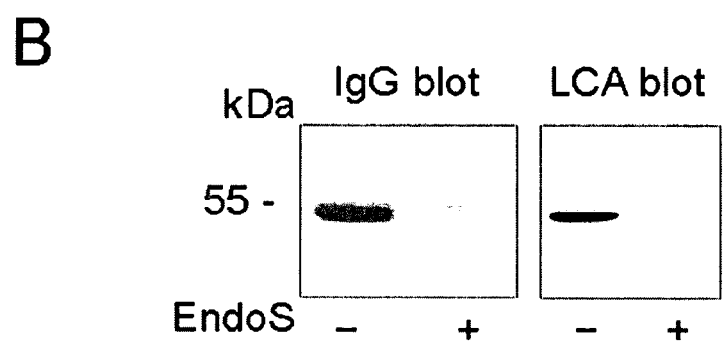
Figure 7:
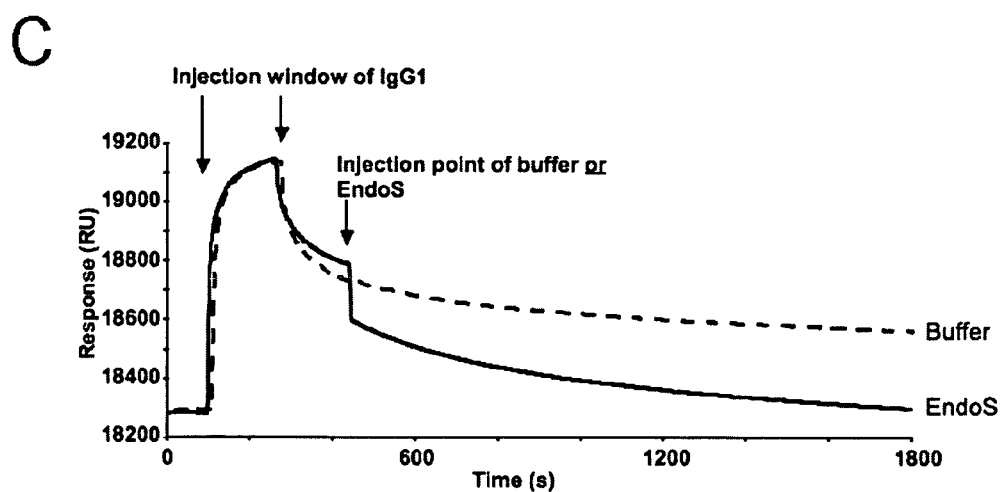

Our experiments this far have revealed that EndoS hydrolysis of IgG inhibits binding to FcγRs on cells and surfaces, but it remained unclear if EndoS has activity on IgG already bound to FcγRs and if such activity could release the IgG bound to FcγRs. Therefore we investigated the effects of EndoS on IgG bound to K562 cells that had been exposed to human plasma and subsequently treated with EndoS. The cell lysates were analyzed by SDS-PAGE and Western blot using an antibody against human IgG. There was significant binding of IgG to K562 cells as judged by results presented in FIG. 7A. Interestingly, no IgG-band was visible on a blot when cells were treated with EndoS, suggesting a total IgG dissociation from the cells (FIG. 7A). A control experiment, using EndoS (E235Q), revealed an IgG signal on the surface of K562 cells comparable to the untreated cells. These results strongly suggest that IgG dissociates from the cell surface due to N-glycan hydrolysis of IgG by EndoS. Similarly, the effect of EndoS on IgG bound to monocytes was analyzed. This showed that most of the monocyte-bound IgG dissociated from cells due to treatment with EndoS as compared to untreated cells (FIG. 7B). As expected, monocytes treated with EndoS, in contrast to control cells, showed no reaction with LCA lectin, indicating that the minute amounts of IgG remaining on the cells as detected in the IgG blot had most likely been hydrolyzed by EndoS (FIG. 7B). The results demonstrated above were further confirmed by surface plasmon resonance experiments. Soluble IgG1 and FcγRII receptor were chosen because of our earlier observation that IgG1 is the strongest binder of FcγRII. After binding of IgG1 to pre-immobilized FcγRIIa, and reaching a steady-state dissociation phase, the IgG1 injection was aborted and replaced by EndoS injection or running buffer. This revealed that EndoS injection causes the dissociation of IgG1 from immobilized FcγRIIa receptor while the IgG1 dissociation from FcγRIIa was unaffected when adding running buffer (FIG. 7C). Taken together these results clearly demonstrate that EndoS by IgG glycan hydrolysis can release IgG bound to FcγRs on cells and surfaces.

Discussion

In the present Example we elucidate the physical interaction between EndoS and IgG and the physiological relevance of EndoS IgG N-glycan hydrolyzing activity for IgG-FcγRs interactions. We present for first time that EndoS specifically acts as an endoglycosidase on all human IgG subclasses, both in purified form and in a plasma environment. As expected, there is a physical interaction between the enzyme and all IgG subclasses, that we successfully demonstrated using enzymatically inactive, mutated form of EndoS. In this study we observed that EndoS hydrolysed IgG did not bind to monocytes, and that there was a nearly completely dissociation of IgG from monocytes upon hydrolysis by EndoS. Since monocytes express FcRI and this receptor has the highest affinity for IgG, we conclude that EndoS influences IgG binding even to FcRI, because the effects of EndoS we observed must be predominantly due to involvement of FcRI. Interestingly, EndoS seems to have an effect on both isotypes of FcγRII receptors, thus influencing both activating and inhibiting IgG mediated effector stimulation.

The above data supports the methods of the invention which utilise EndoS polypeptides. EndoS polypeptides having IgG endoglycosidase activity could be used for in vitro treatment of samples such as whole blood or purified blood cells in order to remove IgG already bound to various FcγRs on these cells. This would facilitate analysis of effects of specific IgG preparations added to the cells, regarding receptor binding and cellular activation, without the interference of pre-bound IgG. EndoS polypeptides lacking IgG endoglycosidase activity but having IgG binding activity, such as EndoS(E235Q) have great potential as a specific IgG purification and detection tool. In this study we have demonstrated that EndoS(E235Q) interacts equally well with all subclasses of IgG. This is comparable to what can be seen for protein G, one of the major molecules currently used for IgG preparation and detection, but advantageous compared to protein A that does not bind IgG3. Furthermore, Protein A also binds IgM and IgA to a certain extent. We have previously shown that there is no interaction between EndoS and IgM or IgA. Furthermore, we could show here that EndoS(E235Q) does not interact with IgG lacking its heavy chain glycans. This is in contrast to both protein G and protein A that binds IgG irrespective of the glycosylation state. This could be especially important when only intact IgG with a functional effector region is required. When using currently available reagents like protein G, a second purification step using for instance a lectin column is required to obtain only the glycosylated fraction of IgG. This property of EndoS(E235Q) could be used in combination with for instance protein G to assess the glycosylation/functional quality of an IgG preparation.

Example 2

Construction of Histidine-Tagged Protein H

Cloning

Nucleotides 124 to 1048 of the structural gene encoding protein H were cloned into the pET21b vector using the restriction sites Not I and Bam HI. The structural gene was obtained using PCR with the vector pHD389 as a template.

The PCR primers used were as follows:

```
5'-TCG GAT CCG GCG CCG GAA GGG GCT AAA ATT GAT

TGG C-3' (37-mer) (SEQ ID NO: 14)

5'-CTC TGC GGC CGC TGC TGT TTC ACC TGT TGA AGG

TAA-3' (36-mer) (SEQ ID NO: 15)
```

The PCR fragment and the vector pET21b were digested with Bam HI and Not I. The digested fragments were separated on a 0.8% agarose gel (E-gel, Invitrogen) and purified with QIAquick Gel Extraction Kit. The PCR fragment was ligated into the vector pET21b using ligase from Invitrogen.

To check the DNA construct, the ligation mix was electroporated into *E. coli* DH10B cells. Five clones were tested using plasmid purification followed by digestion with Bam HI and Not I. Positive colonies were picked and grown for plasmid purification. The plasmid was transferred into *E. coli* BL21 for effective protein expression.

Protein Expression and Purification

Protein expression was performed using standard protocol and instructions for expression using the pET21b vector. The cells were harvested, resuspended in buffer and sonicated. The cell debris was discarded using centrifugation and clear lysate was added onto a 1 ml HisTrap column from Amersham BioSciences using standard protocol. The protein eluated from the column was analysed using electrophoresis under reduced conditions using NuPage 4-12% BisTris gel (Invitrogen). The molecular weight of the protein was approx 35 kDa; the theoretical molecular weight of HisProtein H is 36 kDa.

IgG binding activity was shown by mixing human IgG and HisProteinH and then capturing the complex on a HisTrap (GE Healthcare) column followed by analysis on NuPage 4-12% BisTris gel (Invitrogen). The eluate contained no IgG fragment, which indicated that IgG was trapped together with the protein H in the column.

Example 3

Construction of Histidine-Tagged IdeS

Cloning

Nucleotides 79 to 1020 of the structural gene encoding IdeS were cloned into the pET21b vector using the restriction sites Xho I and Bam HI. The structural gene was obtained using PCR on the pGEX:IdeS vector.

The PCR primers used were as follows:

```
5'-CCG GAT CCG CTA GCA GAT AGT TTT TC-3' (26-mer)
(SEQ ID NO: 16)

5'-GGC CTC GAG GGA ATT GGT CTG ATT CC-3' (26-mer)
(SEQ ID NO: 17)
```

The PCR fragment and the vector pET21b were digested with Bam HI and Xho I. The digested fragments were separated on a 0.8% agarose gel (E-gel, Invitrogen) and purified with QIAquick Gel Extraction Kit. The PCR fragment was ligated into the vector pET21 busing ligase from Invitrogen.

To check the DNA construct, the ligation mix was electroporated into *E. coli* DH10B cells. Five clones were tested using plasmid purification followed by digestion with Bam HI and Xho I. Positive colonies were picked and grown for plasmid purification. The plasmid was transferred into *E. coli* BL21 for effective protein expression.

Protein Expression and Purification

Protein expression was performed using standard protocol and instructions for expression using the pET21b vector. The cells were harvested, resuspended in buffer and sonicated. The cell debris was discarded using centrifugation and clear lysate was added onto a 1 ml HisTrap column from Amersham BioSciences using standard protocol. The protein eluted from the column was analysed using electrophoresis under reduced conditions using NuPage 4-12% BisTris gel (Invitrogen). The expressed and purified protein was analysed using electrophoresis with NuPage 4-12% BisTris gel (Invitrogen). The molecular weight of the protein was approximately 34 kDa.

IdeS activity was tested by mixing human IgG and IdeS for 1 hour at 37° C. The result was evaluated under reduced conditions with electrophoresis using a NuPage 4-12% BisTris gel (Invitrogen). Pure HisIdeS and pure IgG were used as references. The gel revealed that the IgG molecule was digested and as a result an additional band at approximately 31 kDa appeared on the gel, corresponding to an IgG cleavage product, as has previously been described (Vincents et al, 2004, Biochemistry 43: 15540-15549).

Example 4

Activity of Histidine-Tagged IdeS in the Presence of Protein H

The following reactions were set up in Eppendorf tubes and the results were analysed with electrophoresis using a NuPage 4-12% BisTris gel (Invitrogen).

| Lane: | Description: | 31 kDa band appearing on the gel: |
|---|---|---|
| 1 | Molecular weight marker | NO |
| 2 | HisIdeS | NO |
| 3 | protein H | NO |
| 4 | IgG | NO |
| 5 | IgG + HisIdeS, incubated for 30 minutes at 37° C. | YES |
| 6 | IgG + HisIdeS + proteinH, incubated for 30 minutes at 37° C. | YES |
| 7 | HisproteinH + IgG, incubated for 30 minutes at 37° C., then HisIdeS was added and incubated for another 30 minutes at 37° C. | YES |

The results above indicated that histidine-tagged IdeS cleaves IgG fractions in the presence of untagged and histidine-tagged protein H.

Example 5

Elution Buffers

The following protocol was used to test different elution buffers for use in the elution of EndoS (E235Q) from IgG sepharose. The buffers tested would be particularly suitable for use in methods of the invention directed towards acid-sensitive antibodies. The different buffers tested were:
1. Sucrose 0.25M, in PBS pH7.4
2. Sucrose 0.5M, in PBS pH7.4
3. Sucrose 0.25M, in PBS pH5.3
4. Sucrose 0.25M, in PBS pH8.5
5. Sucrose 0.25M, Maltose 0.25M, in PBS pH7.4
6. PBS, pH7.4

IgG-sepharose gels were made according to standard protocols and washed using PBS pH7.4. For each tested elution buffers, 0.3 mg of GST-tagged EndoS (E235Q) was loaded onto the gel as a test sample. The samples were incubated on a rocking table for 1 h and supernatants removed by centrifugation at 500 g for 3 minutes. The samples were washed with 4×1.0 ml PBS, pH7.4. GST-tagged EndoS (E235Q) was then eluted using 1.0 ml of an elution buffer selected from 1-6 above. Each of 1-6 was tested on a separate sample. All samples were incubated on rocking table for 1.5 h. The first eluate (Eluate 1) was then removed by centrifugation at 500 g for 3 minutes. An additional 1.0 ml of the respective elution buffers was added to each sample, and the samples were incubated on rocking table for approximately 30 min. The second eluate (Eluate 2) was removed by centrifugation as described above. A final, additional 1.0 ml of the respective elution buffers was added to each sample, and the samples were incubated on rocking table for approximately 50 min. The final eluate (Eluate 3) was removed by centrifugation as described above.

All eluates from each sample, and the original supernatants, were then diluted in 300 μPBS before analysis by gel electrophoresis (not shown).

The gel analysis demonstrated that GST-tagged EndoS (E235Q) could be eluted from IgG using different concentrations and types of saccharide as eluents. The elution buffers with sucrose at 0.25 and 0.5M were the most effective.

The invention claimed is:

1. A method of assessing the glycosylation state or functional quality of an IgG containing sample, which method comprises taking a first and a second sub-sample of the IgG-containing sample, and wherein steps (a) and (b) as set out below are applied to the first sub-sample, and steps (a) and (b) as set out below are applied to the second sub-sample except the EndoS polypeptide is substituted with an alternative IgG-binding reagent which is capable of binding unglycosylated and/or denatured, inactive IgG, wherein steps (a) and (b) are:

(a) contacting said IgG-containing sample with an EndoS polypeptide which lacks IgG endoglycosidase activity, to thereby allow formation of a IgG-EndoS polypeptide complex;

(b) separating said EndoS from the contacted sample;

and wherein the method further comprises:

(c) quantifying the amount of IgG bound to the EndoS polypeptide in the first sub-sample, and the amount of IgG bound to the alternative IgG-binding reagent in the second sub-sample; and (d) comparing both of the amounts of bound IgG determined in (c);

and thereby assessing the glycosylation state or functional quality of an IgG containing sample, wherein said EndoS polypeptide which lacks IgG endoglycosidase activity is:

(i) the EndoS polypeptide having the amino acid sequence of SEQ ID NO: 2; or (ii) a fragment of (i) containing residues 191 to 199 of SEQ ID NO: 2; or (iii) a fragment of (iii) in which said residues 191 to 199 of SEQ ID NO: 2 have one or more conservative substitutions, provided that glutamic acid is not present at position 199;

and wherein each of (i), (ii) and (iii) has IgG-binding activity.

2. Method according to claim 1 wherein the alternative IgG-binding reagent comprises Protein G and/or Protein A.

3. Method according to claim 1 wherein the fragment of (ii) consists of amino acids 1 to 409 of SEQ ID NO: 2.

* * * * *

UNITED STATES PATENT AND TRADEMARK OFFICE
CERTIFICATE OF CORRECTION

PATENT NO. : 8,323,908 B2
APPLICATION NO. : 12/677680
DATED : December 4, 2012
INVENTOR(S) : Maria Allhorn et al.

It is certified that error appears in the above-identified patent and that said Letters Patent is hereby corrected as shown below:

In column 2, cover page, 3rd Collin Reference, delete "*Inspection*" and insert --*Infection*--;
In column 68, Claim 1, line 23, delete "a" and insert --the--;
In column 68, Claim 1, line 23, after the word of, delete "iii" and insert --ii--.

Signed and Sealed this
Fifth Day of March, 2013

Teresa Stanek Rea
*Acting Director of the United States Patent and Trademark Office*